United States Patent
Matsukawa et al.

(10) Patent No.: US 9,347,949 B2
(45) Date of Patent: May 24, 2016

(54) ISOTOPE-LABELED PYRYLIUM COMPOUND

(71) Applicants: NATIONAL UNIVERSITY CORPORATION UNIVERSITY OF FUKUI, Fukui-shi, Fukui (JP); HOKURIKU UNIVERSITY, Kanazawa-shi, Ishikawa (JP); TAIYO NIPPON SANSO CORPORATION, Tokyo (JP)

(72) Inventors: Shigeru Matsukawa, Fukui (JP); Kazumi Narita, Fukui (JP); Yasushi Arakawa, Kanazawa (JP); Haruki Shimodaira, Tokyo (JP)

(73) Assignees: National University Corporation University of Fukui, Fukui (JP); Hokuriku University, Kanazawa (JP); Taiyo Nippon Sanso Corporation, Tokyo (JP)

( * ) Notice: Subject to any disclaimer, the term of this patent is extended or adjusted under 35 U.S.C. 154(b) by 0 days.

(21) Appl. No.: 14/389,149

(22) PCT Filed: Mar. 28, 2013

(86) PCT No.: PCT/JP2013/059405
§ 371 (c)(1),
(2) Date: Sep. 29, 2014

(87) PCT Pub. No.: WO2013/147096
PCT Pub. Date: Oct. 3, 2013

(65) Prior Publication Data
US 2015/0094233 A1    Apr. 2, 2015

(30) Foreign Application Priority Data

Mar. 30, 2012 (JP) .................. 2012-079110

(51) Int. Cl.
*C07D 309/34* (2006.01)
*G01N 33/58* (2006.01)
*G01N 33/74* (2006.01)
*G01N 33/68* (2006.01)
*H01J 49/00* (2006.01)

(52) U.S. Cl.
CPC .......... *G01N 33/6848* (2013.01); *C07D 309/34* (2013.01); *G01N 33/58* (2013.01); *G01N 33/6806* (2013.01); *G01N 33/74* (2013.01); *G01N 2458/15* (2013.01); *G01N 2560/00* (2013.01); *G01N 2570/00* (2013.01); *H01J 49/00* (2013.01)

(58) Field of Classification Search
CPC ..... C07D 309/34; G01N 33/58; G01N 33/74; G01N 33/68
See application file for complete search history.

(56) References Cited

U.S. PATENT DOCUMENTS 4,642,359 A    2/1987   Rajoharison et al.
2010/0190261 A1  7/2010   Matsukawa

FOREIGN PATENT DOCUMENTS

WO    WO 2008/156139 A1    12/2008

OTHER PUBLICATIONS

Barltrop et al. (full), Journal of the Chemical Society, Chemical Communications 1980, 13, 606-608.*
Barltrop et al. (abstract), 1980, caplus an 1980:638417.*
Hofelschweiger, Biance, "The Pyrylium Dyes: A New Class of Biolabels. Synthesis, Spectroscopy, and Application as Labels and in General Protein Assay", Dissertation for Doctoral Degree in Natural Sciences provided to the Faculty of Chemistry and Pharmacy at the University of Regensburg, pp. 1-136 [retrieved from URL: http://epub.uni-regensburg.de/10331/1/Dissertation.pdf] (Jun. 2005).
European Patent Office, Supplementary European Search Report in European Patent Application No. 13767425 (Mar. 19, 2015).
Balaban, A., *Journal of Labelled Compounds and Radiopharmaceuticals*, 18(11): 1621-1632 (1981).
Balaban et al., *Journal of Organic Chemistry*, 69(2): 536-542 (2004).
Dimroth et al., *Chemische Berichte*, 114(9): 3004-3018 (1981).
Japanese Patent Office, International Search Report in International Patent Application No. PCT/JP2013/059405 (Jun. 11, 2013).
The International Bureau of WIPO, International Preliminary Report on Patentability in International Patent Application No. PCT/JP2013/059405 (Oct. 1, 2014).

* cited by examiner

*Primary Examiner* — Sun Jae Yoo
(74) *Attorney, Agent, or Firm* — Leydig, Voit & Mayer, Ltd.

(57) ABSTRACT

The present invention provides a compound represented by the formula (I):

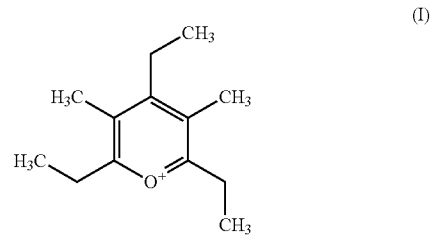

or a salt thereof; and a method of quantitatively analyzing an amino group-containing target substance, including labeling a target substance in samples by using, as a labeling compound, two or more of such compounds having a mutually different mass due to isotope labeling, to confer a mass difference to the target substance between two or more samples, and the like.

22 Claims, 15 Drawing Sheets

Fig. 5

| BSA peptide seq. | quant. ratio | | |
|---|---|---|---|
| | PyII-6/PyII-0 | PyII-12/PyII-0 | PyII-12/PyII-6 |
| CASIQKFGER | 2.24 | 3.68 | 1.64 |
| CCTKPESER | 2.61 | 4.07 | 1.56 |
| ETYGDMADCCEKQEPER | 2.69 | 4.47 | 1.66 |
| KVPQVSTPTLVEVSR | 2.57 | 3.93 | 1.53 |
| average measured value | 2.53 | 4.04 | 1.60 |
| theoretical value | 2.5 | 4.0 | 1.6 |

| Transferrin peptide seq. | quant. ratio | | |
|---|---|---|---|
| | PyII-6/PyII-0 | PyII-12/PyII-0 | PyII-12/PyII-6 |
| DDTVCLAKLHDR | 0.66 | 0.28 | 0.43 |
| KCSTSSLLEACTFR | 0.58 | 0.21 | 0.37 |
| KPVEEYANCHLAR | 0.62 | 0.25 | 0.40 |
| MDAKMYLGYEYVTAIR | 0.53 | 0.15 | 0.28 |
| SETKDLLFR | 0.61 | 0.22 | 0.36 |
| TAGWNIPMGLLYNKINHCR | 0.61 | 0.25 | 0.41 |
| WCAVSEHEATKCQSFR | 0.64 | 0.27 | 0.42 |
| average measured value | 0.61 | 0.23 | 0.38 |
| theoretical value | 0.625 | 0.25 | 0.4 |

Fig. 6

Preparation ○ PyII reagent preparation each PyII reagent 4-5 mg
↓ ← prepared to about 200 mM with Milli-Q about 100 µL
Abs, 285 nm measurement ⇒ slight adjustment of concentration
　　　　　　　　　　　　　　　　to afford same absorbance day 1 ○ PyII introduction 30 µL 100 µg/100 µL plasma protein CLS solution
 62.8 µL CLS (7M Urea, 3M thioUrea, 2% CHAPS
        , 50 mM Na Borate PH9.5)
 7.2 µL 200 mM PyII reagent (3 kinds)

100 µL
↓
50°C, 4 hr
↓
acetone precipitation (Merck kit)
↓
washing twice, centrifugation, air drying day 2 ○ reduction alkylation, trypsin digestion air drying protein + 30 µL CLS
　↓
　PyII-0, PyII-6, PyII-12-labeled products, each 10 µL
　　　　　collected and mixed (30 µL)
　↓← 3.3 µL DTT
　50°C, 1 hr
　↓← 3.3 µL IAA
　37°C, 30 min
　↓← 10 mM Tris (PH 7.4) 240 µL
　↓← 6 µg trypsin
　37°C, over night day 3 ○ SCX fractionation, desalting ↓← adjusted to pH2-3 with several µL of 1N HCl
　SCX fractionation
　↓
　desalting after which MS measurement Fig. 8
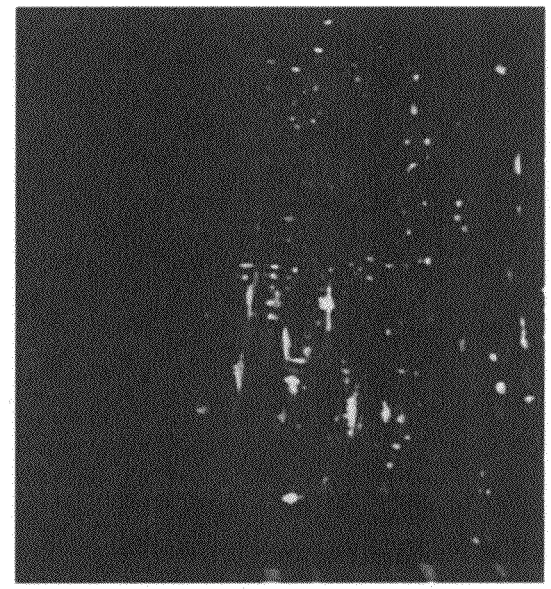
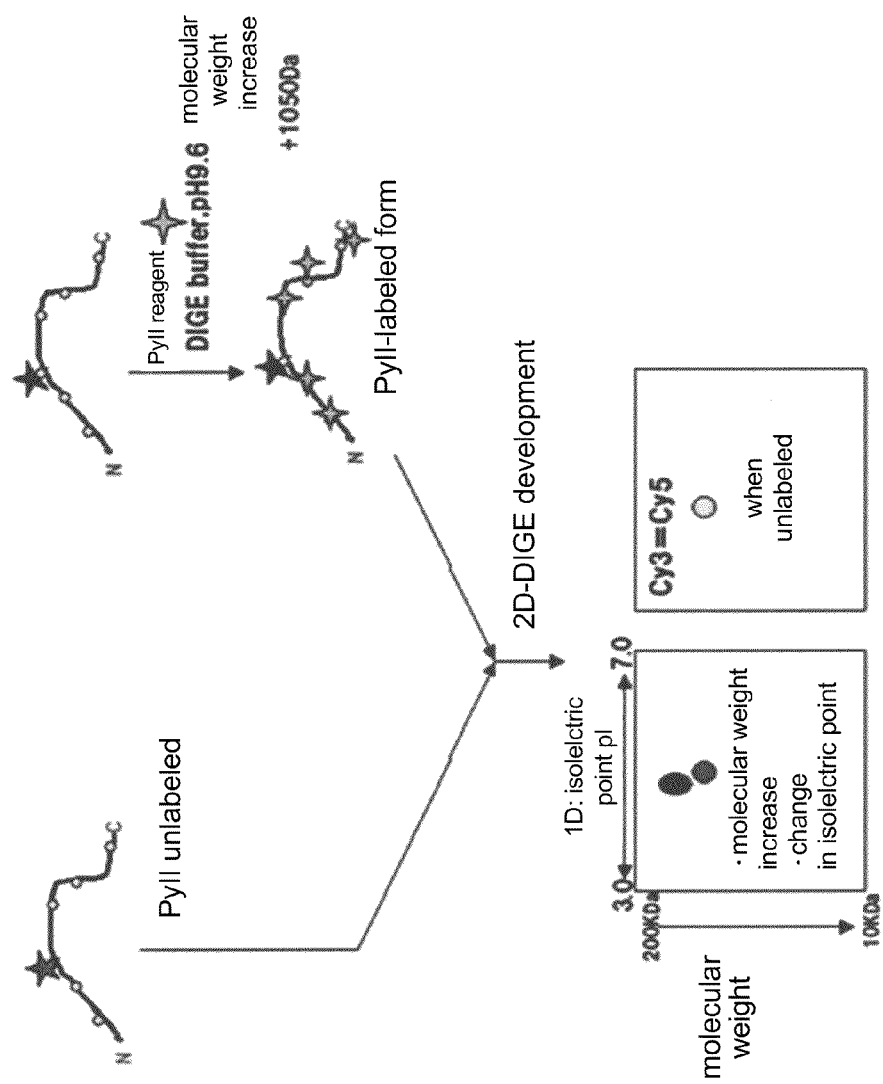

ISOTOPE-LABELED PYRYLIUM COMPOUND

CROSS-REFERENCE TO RELATED APPLICATIONS

This patent application is the U.S. national phase of International Patent Application No. PCT/JP2013/059405, filed Mar. 28, 2013, which claims the benefit of Japanese Patent Application No. 2012-079110, filed on Mar. 30, 2012, which are incorporated by reference in their entireties herein.

TECHNICAL FIELD

The present invention generally relates to the analysis of biological samples. More particularly, the present invention relates to a novel isotope-labeled pyrylium compound, and a method of quantitatively analyzing an amino group-containing compound in two or more samples by mass spectrometry and using the compound, and the like.

BACKGROUND ART

For the analyses of proteins, one of the present inventors reported a method of using a compound represented by the following formula:

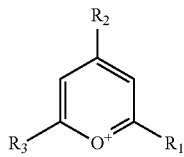

wherein $R_1$, $R_2$ and $R_3$ are the same or different and each is hydrogen, halogen or alkyl, or a salt thereof as a labeling compound (patent document 1). Specifically, three compounds represented by the following formulas:

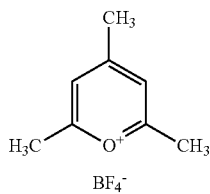
Py0

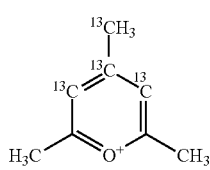
Py4

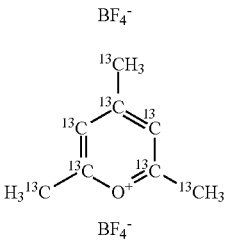
Py8 which have mass difference from each other due to isotope labeling (which are generically referred to as Py compound) have been synthesized. In the method described in the document, a protein in two or more analysis samples are labeled with any of the Py compounds to confer a mass difference to the same protein among samples, the samples are mixed, and the protein is hydrolyzed. The obtained labeled peptide is subjected to mass spectrometry to identify the protein from which it derives by structural analysis of the peptide, and the presence ratio of the identified protein among samples is further calculated based on the mass spectrum.

On the other hand, conventional analysis of amino acid employs a quantification method including mutual separation of 20 or more kinds of biological amino acids by one performance of high performance liquid chromatography (HPLC) analysis, reacting the amino acids with ninhydrin, and quantifying the amino acids based on the absorbances of the resultant products. However, the sensitivity of this method is low, and is not suitable for the analysis of an amino acid at a low concentration.

To achieve higher sensitivity, therefore, use of a fluorescent label has been proposed, which realizes about 10-fold or higher sensitivity.

Furthermore, for an amino acid present at a low concentration undetectable even thereby, a method including separation using liquid chromatography followed by mass spectrometry is adopted. In this case, to facilitate ionization of separated amino acids, amino acids are derivatized using a reagent that reacts with an amino group, and then subjected to liquid chromatographic separation and mass spectrometry. However, even when this method is used, the conventional technique has a limitation in highly sensitive analysis.

Patent document 2 describes a method of producing various pyrylium compounds. It is stated that the formula described in the document produces two kinds of isomers; however, since separation of the both is not easy, the detection relies on the NMR analysis of a pyridine compound produced by a reaction with ammonia and that an acid usable for the reaction has Ho of −10 to −5.

DOCUMENT LIST

Patent Documents patent document 1: WO 2008/156139
patent document 2: U.S. Pat. No. 4,642,359

SUMMARY OF THE INVENTION

Problems to be Solved by the Invention

In the analysis of proteins, a peptide to be subjected to mass spectrometry often has a molecular weight within the range of 500-3000 Da. Therefore, due to naturally-present isotopes, the mass spectrum of such peptide is observed as plural peaks having a mass difference from each other rather than a single peak. While the size of each peak depends on the molecular weight of peptide, since a monoisotopic peak is the main peak, the peak at a position having a mass larger by 1 to 3 is large and the peak thereafter becomes gradually small. Therefore, as in the method of the above-mentioned patent document 1, when a mass difference is conferred to the same peptide by using two or more labeling compounds having a mass difference from each other due to labeling with an isotope and the mass difference is small, interference occurs between different peaks and the analysis becomes complicated. The present inventors have empirically found that interference cannot be ignored between the monoisotopic peak and a peak with a mass difference of 4, but mutual interference can be ignored when the mass difference is 6. For protein analysis, therefore, the development of an isotope reagent having a largest possible mass difference has been desired.

On the other hand, from the current situation of the analysis techniques for amine and amino acid, a method capable of quantifying amine and amino acid in biological samples with higher sensitivity is desired. In addition, a technique capable of comprehensively analyzing amine, amino acid and the like present in each sample by multiple quantification of plural biological samples has been desired.

Means of Solving the Problems

The present inventors have conducted intensive studies in an attempt to solve the above-mentioned problems. For this end, the present inventors first searched for a better compound for protein labeling by using a Py compound as a leading compound. As a result, they have found that a pyrylium compound having an ethyl group at the 2-position, the 4-position and the 6-position, and further, a methyl group at the 3-position and the 5-position has superior properties such as reactivity with protein, water solubility and the like. Thus, they further tried synthesis of the isotope-labeled compound and succeeded in the synthesis of 3 kinds of compounds mutually having a mass difference of 6 (the below-mentioned PyII-0, PyII-6 and PyII-12) at a high purity. Using the obtained isotope-labeled compounds, specifically PyII-0, PyII-6 and PyII-12, they tried quantitative analysis of proteins in the same manner as in the above-mentioned patent document 1, and confirmed that highly sensitive multiple quantitative analysis can be performed using these isotope-labeled compounds, an overlap between peaks in the mass spectrum is less since the mass difference among the compounds is 6, and quantification accuracy can be strikingly improved.

The present inventors have further tried to apply the compound to the analysis of an amino group-containing non-peptidic compound such as amine, amino acid and the like. In the analysis of an amino group-containing non-peptidic compound, an interference between peaks can be avoided when the mass difference between labeling compounds is 2. Therefore, it is advantageous for analysis efficiency to prepare as many kinds as possible of isotope-labeled compounds having a mutual mass difference of 2. They have further conducted synthesis experiments, and succeeded in the synthesis of compounds having a mass difference of 2, 4, 8 or 10 relative to the above-mentioned PyII-0 (the below-mentioned PyII-2, PyII-4, PyII-8, PyII-10) at a high purity. They have found that analysis by using these isotope-labeled compounds enables not only detection of an amino group-containing non-peptidic compound in a biological sample with high sensitivity, but also comprehensive analysis of an amino group-containing non-peptidic compound contained in each sample by simultaneous quantification of plural samples. In addition, the present inventors confirmed that a Py derivative of an amino group-containing non-peptidic compound shows low bindabiliy to a trap column (ODS column) once introduced before introduction into an analysis column, which column is essential in nano-liquid chromatography system, and therefore, it is not easy to apply the derivative to a high sensitivity automatic analysis using an Autosampler. However, it was found that a PyII compound creates a possibility of automated highly sensitive analysis of an amino group-containing non-peptidic compound by utilizing an ODS column as a trap column, since the PyII compound shows high hydrophobicity of the side chain of the ring as compared to the Py compound and contributes to the improvement of the hydrophobicity adsorption capacity.

The present inventors have conducted further considerations based on the above-mentioned findings and completed the present invention.

Accordingly, the present invention provides the following.

[1] A compound represented by the formula (I):

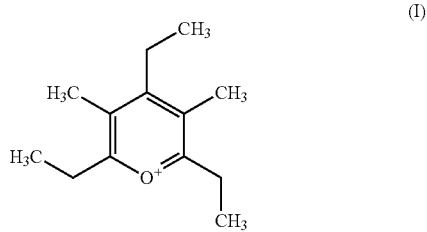

or a salt thereof.

[2] The compound of the above-mentioned [1], wherein the formula (I) has one or more carbon atoms having a mass number of 13, or a salt thereof.

[3] The compound of the above-mentioned [1], which is one compound selected from the group consisting of PyII-0, PyII-2, PyII-4, PyII-6, PyII-8, PyII-10 and PyII-12 represented by the formulas (II):

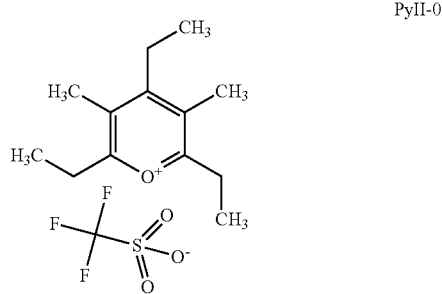

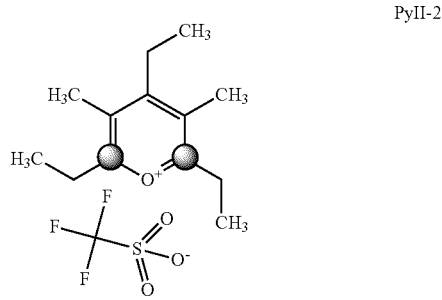

-continued

PyII-4
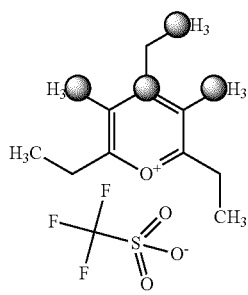

PyII-6
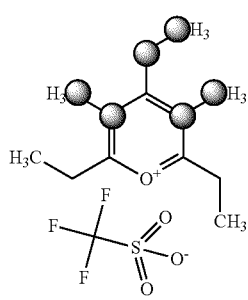

PyII-8
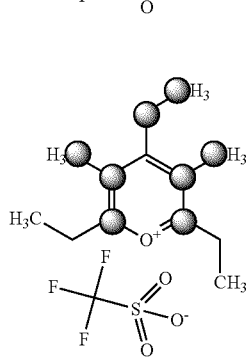

PyII-10
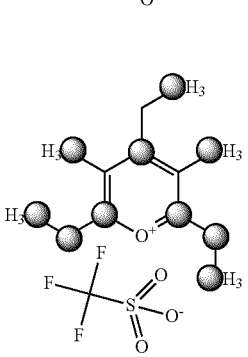

PyII-12
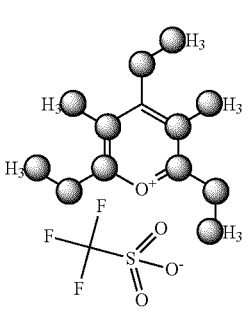

wherein carbon atoms shown by black balls have a mass number of 13, or a salt thereof.

[4] A kit for quantifying an amino group-containing target substance in a biological sample by using a mass spectrometer, which comprises, as a labeling compound, two or more compounds having a mutually different mass due to isotope labeling, which are represented by the formula (I):

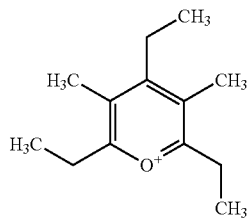
(I)

or a salt thereof.

[5] The kit of the above-mentioned [4], comprising two or more compounds represented by the formula (I) having a mass difference of not less than 6 or a salt thereof, wherein the target substance is a protein.

[6] The kit of the above-mentioned [5], comprising a compound represented by the formula (I), which does not contain a carbon atom having a mass number of 13, a compound represented by the formula (I), which has 6 carbon atoms having a mass number of 13, and a compound represented by the formula (I), which has 12 carbon atoms having a mass number of 13, or a salt thereof.

[7] The kit of the above-mentioned [6], comprising PyII-0, PyII-6 and PyII-12 represented by the formula (III):

(III)

PyII-0
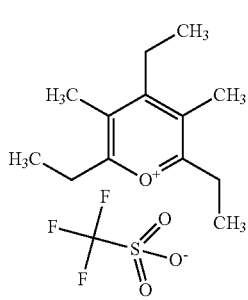

PyII-6
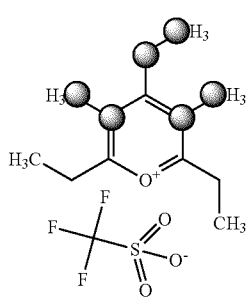

PyII-12

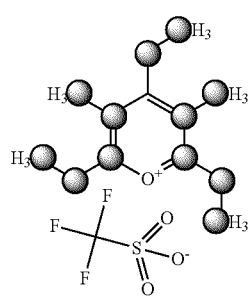

wherein carbon atoms shown by a black ball have a mass number of 13.

[8] The kit of the above-mentioned [4], comprising two or more compounds represented by the formula (I) having a mass difference of two or more or a salt thereof, wherein the target substance is an amino group-containing non-peptidic compound.

[9] The kit of the above-mentioned [8], comprising two or more compounds selected from the group consisting of a compound represented by the formula (I), which does not contain a carbon atom having a mass number of 13, a compound represented by the formula (I), which has 2 carbon atoms having a mass number of 13, a compound represented by the formula (I), which has 4 carbon atoms having a mass number of 13, a compound represented by the formula (I), which has 6 carbon atoms having a mass number of 13, a compound represented by the formula (I), which has 8 carbon atoms having a mass number of 13, a compound represented by the formula (I), which has 10 carbon atoms having a mass number of 13, and a compound represented by the formula (I), which has 12 carbon atoms having a mass number of 13, or a salt thereof.

[10] The kit of the above-mentioned [9], comprising two or more compounds selected from the group consisting of PyII-0, PyII-2, PyII-4, PyII-6, PyII-8, PyII-10 and PyII-12 represented by the formulas (II):

(II)

PyII-0

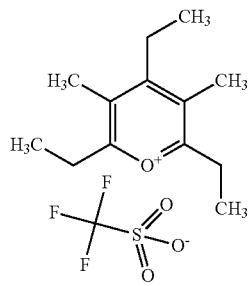

PyII-2

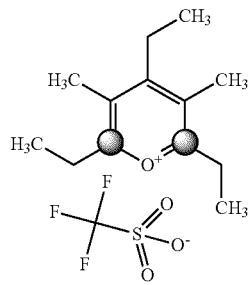

PyII-4

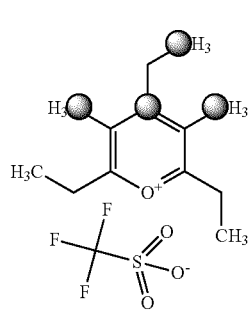

PyII-6

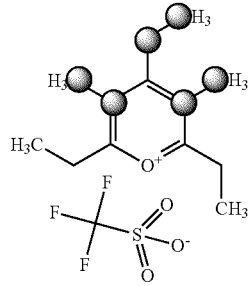

PyII-8

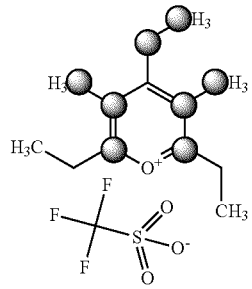

PyII-10

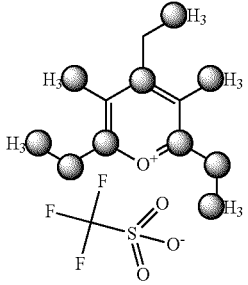

-continued

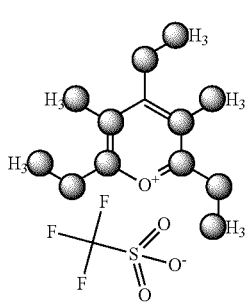
PyII-12 wherein carbon atoms shown by a black ball have a mass number of 13.

[11] A method of quantitatively analyzing an amino group-containing target substance in two or more biological samples by using a mass spectrometer, comprising
(1) a step of preparing two or more biological samples to be subjected to an analysis,
(2) a step of labeling a target substance in samples prepared by using, as a labeling compound, two or more compounds having a mutually different mass due to isotope labeling, which are represented by the formula (I):

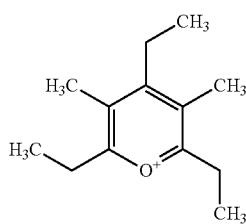
(I)

or a salt thereof, to confer a mass difference to the target substance between the samples,
(3) a step of preparing a mixture from all samples subjected to the labeling, and
(4) a step of subjecting the mixture to mass spectrometry, determining a presence ratio of the target substance in the mixture based on the ratio of peak intensity in mass spectrum of a target substance mutually having a mass difference due to labeling, and determining a quantitative ratio of the target substance between samples subjected to the preparation of the mixture, from the obtained presence ratio and the mixing ratio of the samples in step (3).
[12] The method of the above-mentioned [11], wherein the target substance is an amino group-containing non-peptidic compound.
[13] The method of the above-mentioned [12], wherein the labeling compound comprises two or more compounds represented by the formula (I) having a mass difference of 2 or more, or a salt thereof.
[14] The method of the above-mentioned [13], wherein the labeling compound comprises two or more compounds selected from the group consisting of
a compound represented by the formula (I), which does not contain a carbon atom having a mass number of 13,
a compound represented by the formula (I), which has 2 carbon atoms having a mass number of 13,
a compound represented by the formula (I), which has 4 carbon atoms having a mass number of 13,
a compound represented by the formula (I), which has 6 carbon atoms having a mass number of 13,
a compound represented by the formula (I), which has 8 carbon atoms having a mass number of 13,
a compound represented by the formula (I), which has 10 carbon atoms having a mass number of 13, and
a compound represented by the formula (I), which has 12 carbon atoms having a mass number of 13,
or a salt thereof.
[15] The method of the above-mentioned [14], wherein the labeling compound comprises two or more compounds selected from the group consisting of PyII-0, PyII-2, PyII-4, PyII-6, PyII-8, PyII-10 and PyII-12 represented by the formulas (II):

(II)

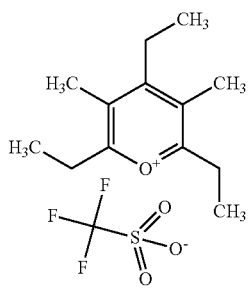
PyII-0

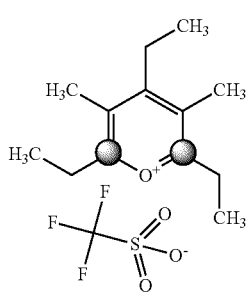
PyII-2

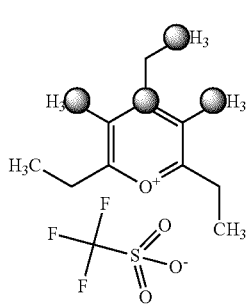
PyII-4

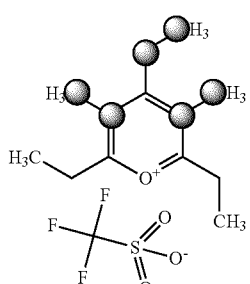
PyII-6

-continued

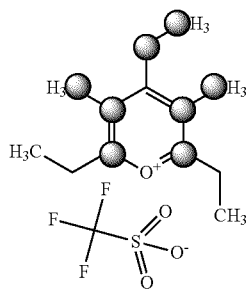
PyII-8

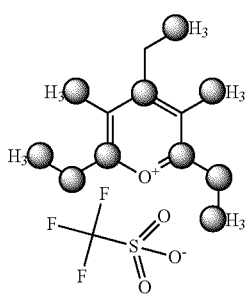
PyII-10

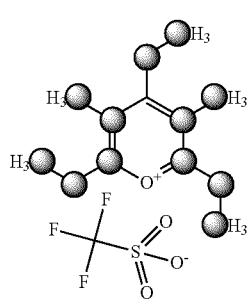
PyII-12 wherein carbon atoms shown by a black ball have a mass number of 13.

[16] The method of the above-mentioned [11], wherein one of the samples prepared in step (1) is the internal standard sample containing a target substance at a known concentration, and the determination of the presence ratio in step (4) comprises determining a ratio of a peak intensity of a target substance derived from each sample other than the internal standard sample and a target substance derived from the internal standard sample.

[17] A method of quantitatively analyzing a protein in two or more biological samples by using a mass spectrometer, comprising (1) a step of preparing two or more biological samples to be subjected to an analysis, (2) a step of labeling a protein in samples prepared by using, as a labeling compound, two or more compounds having a mutually different mass due to isotope labeling, which are represented by the formula (I):

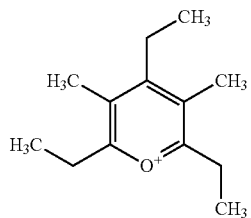
(I)

or a salt thereof, to confer a mass difference to the same protein between the samples, (3) a step of preparing a mixture from all samples subjected to the labeling, (4) a step of digesting the protein in the mixture with a protease to give a peptide, (5) a step of subjecting the obtained peptide to mass spectrometry, and determining a presence ratio of the peptide in the mixture based on the ratio of peak intensity in mass spectrum of the peptide mutually having a mass difference due to labeling, and (6) a step of identifying a protein from which the peptide having the determined presence ratio derives, and determining a quantitative ratio of the protein between samples subjected to the preparation of the mixture, from the presence ratio and the mixing ratio of the samples in step (3).

[18] The method of the above-mentioned [17], wherein the labeling compound comprises two or more compounds represented by the formula (I) having a mass difference of 6 or more, or a salt thereof.

[19] The method of the above-mentioned [18], wherein the labeling compound comprises a compound represented by the formula (I), which does not contain a carbon atom having a mass number of 13, a compound represented by the formula (I), which has 6 carbon atoms having a mass number of 13, and a compound represented by the formula (I), which has 12 carbon atoms having a mass number of 13 or a salt thereof, and the protein in 3 biological samples is quantitatively analyzed.

[20] The method of the above-mentioned [19], wherein the labeling compound comprises PyII-0, PyII-6 and PyII-12 represented by the following formulas (III):

(III)

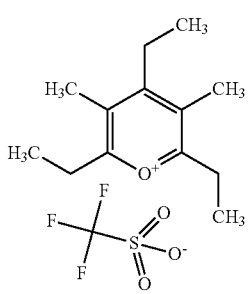
PyII-0

PyII-6

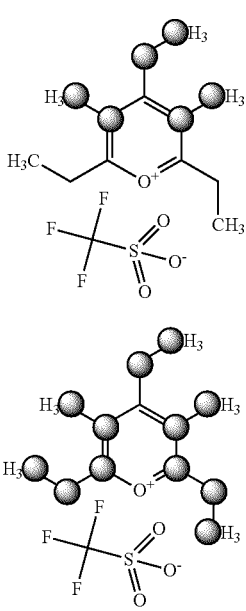

PyII-12

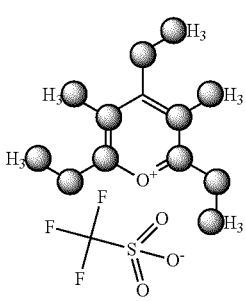

wherein carbon atoms shown by a black ball have a mass number of 13.

[21] The method of the above-mentioned [17], wherein one of the samples prepared in step (1) is the internal standard sample obtained by mixing all other prepared samples, and the determination of the presence ratio in step (5) comprises determining a ratio of a peak intensity of a peptide derived from each sample other than the internal standard sample and a peptide derived from the internal standard sample.

[22] A method of producing a compound of the formula (I) or a salt thereof, comprising condensing 3-ethyl-3-pentanol or 3-ethyl-2-pentene with anhydrous propionic acid in the presence of an anhydrous acid to give a compound of the formula (I):

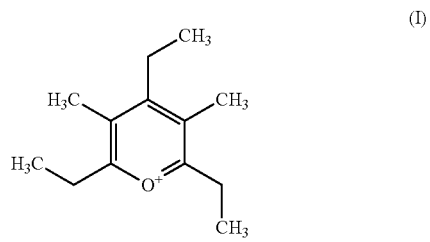
(I)

or a salt thereof.

[23] A compound represented by the formula (IV):

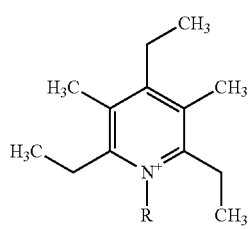
(IV)

wherein R is any optionally substituted hydrocarbon group (excluding a compound having a peptide bond), or a salt thereof.

Effect of the Invention

Since the isotope labeling compound of the present invention can provide plural compounds having a large mass difference (e.g., not less than 6) relative to each other, it can solve the problem of mutual interference between isotope peaks in comprehensive expression difference analysis of protein even with a peptide having a comparatively high molecular weight. Particularly, there is no conventional stable isotope-labeling reagent capable of providing 3 kinds of compounds having a mass difference of 6. According to the present invention, however, 3 kinds of stable isotope-labeled reagents having a mass difference of 6 are provided, and highly sensitive multiple simultaneous protein quantitative analysis can be performed among 3 samples by mass spectrometry, which is conducible to an exceptionally efficient quantitative analysis of proteins.

The isotope labeling compound of the present invention also enables a simultaneous highly sensitive analysis of amino group-containing non-peptidic compounds contained in plural samples (e.g., 7 kinds). Furthermore, by automation using a trap column, a system capable of automatically performing a highly sensitive analysis at a femto mol level for 24 hr can be constructed.

BRIEF DESCRIPTION OF THE DRAWINGS

FIG. 5 shows intensity ratios of PyII-0-labeled peptide-derived peak, PyII-6-labeled peptide-derived peak, and PyII-12-labeled peptide-derived peak in the mass spectrum of FIG. 4 (upper panel: BSA, lower panel: TRFE).

FIG. 6 shows an exemplary protocol of a verification experiment using a human plasma real sample by a comparison quantification method using a PyII reagent.

FIG. 8 shows the outline of an experimental verification method of protein labeling with PyII reagent by the fluorescence DIGE method (left Figure), and the results of two-dimensional electrophoresis of the total protein extracted from two color fluorescence-labeled HeLa cells (right Figure).

FIG. 12-1 shows an ion chromatograph of PyII derivatives of 8 kinds of amine/amino acids.

FIG. 12-2 shows an ion chromatograph of PyII derivatives of 8 kinds of amine/amino acids.

FIG. 12-3 shows an ion chromatograph of PyII derivatives of 8 kinds of amine/amino acids.

FIG. 12-4 shows an ion chromatograph of PyII derivatives of 8 kinds of amine/amino acids.

FIG. 13-1 shows the mass spectrum of the peak portion of FIG. 12.

FIG. 13-2 shows the mass spectrum of the peak portion of FIG. 12.

FIG. 13-3 shows the mass spectrum of the peak portion of FIG. 12.

DESCRIPTION OF EMBODIMENTS

Figure 1:
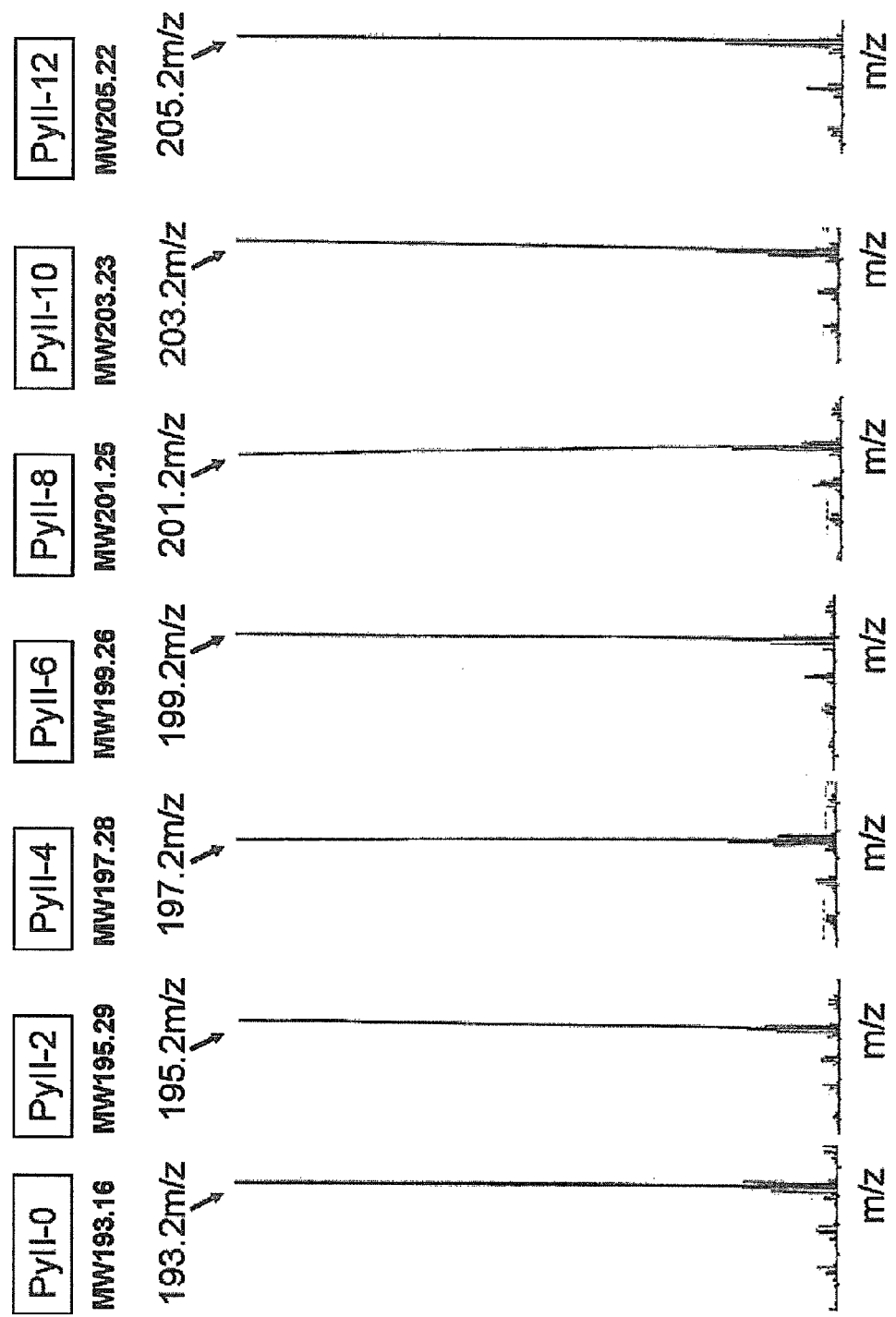
FIG. 1 shows EI-MS spectrum of each synthesized PyII compound.

The present invention is explained in detail in the following.

(Isotope Labeling Compound)

The present invention provides a compound represented by the following formula (I):

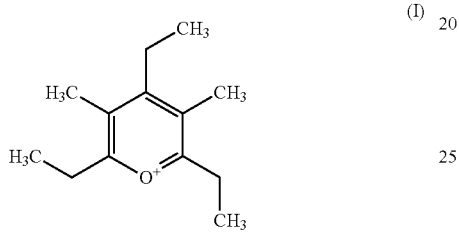

(I)

or a salt thereof. The compound or a salt thereof can be labeled with one or more (e.g., 1, 2, 3, 4, 5, 6, 7, 8, 9, 10, 11, 12, 13) isotopes by, for example, a carbon atom having a mass number of 13. Hereinafter, a compound represented by the formula (I) or a salt thereof, including those not labeled with an isotope, is also referred to as the isotope labeling compound of the present invention.

The isotope labeling compound of the present invention is generally utilized in the form of a salt. The salt may be any anion atom or anion molecule as long as it does not prevent an amino group labeling reaction. Examples thereof include trifluoromethanesulfonate, hexafluorophosphate, tetrafluoroborate, perchlorate, trimethylsilyl trifluoromethanesulfonate, methanesulfonate and the like, particularly preferably trifluoromethanesulfonate having good crystallinity of salt and comparatively high safety. In addition, hexafluorophosphate can be easily obtained by adding sodium hexafluorophosphate to tetrafluoroborate.

Preferable examples of the isotope labeling compound of the present invention include PyII-0, PyII-2, PyII-4, PyII-6, PyII-8, PyII-10 and PyII-12 represented by the following formulas (II):

(II)

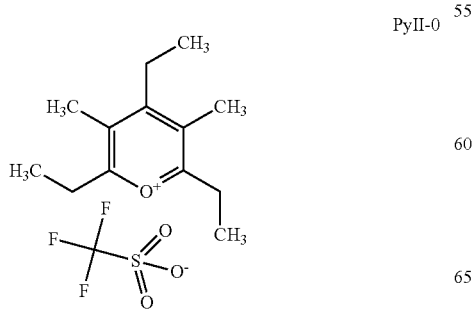

PyII-0

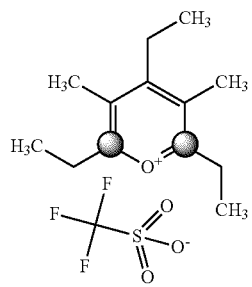

PyII-2

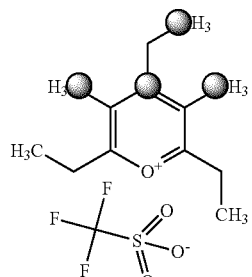

PyII-4

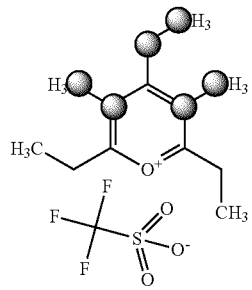

PyII-6

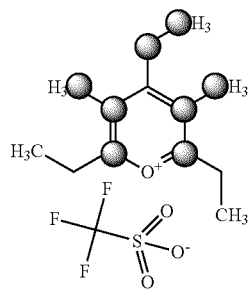

PyII-8

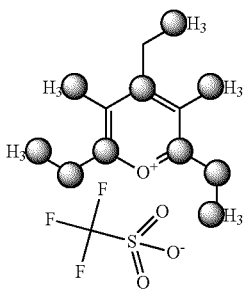

PyII-10

-continued

PyII-12

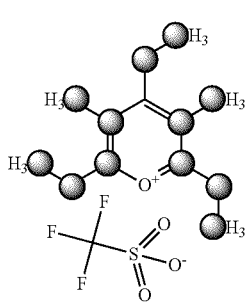

wherein carbon atoms shown by a black ball have a mass number of 13 (hereinafter to be also generically referred to as compound PyII).

The isotope labeling compound of the present invention can be obtained by condensing 3-ethyl-3-pentanol or 3-ethyl-2-pentene with anhydrous propionic acid in the presence of anhydrous acid. According to the production method of the present invention, since a single compound is produced without developing an isomer, a separation operation thereafter is convenient.

Examples of the anhydrous acid include trifluoromethanesulfonic acid, hexafluorophosphoric acid, tetrafluoroboric acid, perchloric acid, trifluoromethanesulfonic acid trimethylsilyl, methanesulfonic acid and the like. Of these, trifluoromethanesulfonic acid showing good crystallinity of salt and comparatively high safety is preferable.

The reaction temperature is generally 40-100° C., preferably 50-65° C., and the reaction time is generally 10 min-24 hr, preferably 1-1.5 hr.

When 3-ethyl-2-pentanol is used, the amount of the starting material compound is generally 3-20 molar equivalents, preferably about 4 molar equivalents, of anhydrous propionic acid relative to 3-ethyl-2-pentanol. The consumption amount of anhydrous propionic acid can be reduced by using 3-ethyl-2-pentene, and specifically, the amount of anhydrous propionic acid can be generally 3-10 molar equivalents, preferably about 3 molar equivalents, relative to 3-ethyl-2-pentene. Anhydrous acid such as trifluoromethanesulfonic acid and the like is generally added in 0.8-1.2 molar equivalents relative to 3-ethyl-2-pentanol or 3-ethyl-2-pentene.

The reaction mixture after the above-mentioned condensation reaction is subjected to concentration, neutralization, extraction and the like by a method known per se, and recrystallized to give a desired compound.

Any isotope labeling compound of the present invention having one or more carbon atoms having a mass number of 13 can also be produced in the same manner as above except that a $^{13}C$-labeled compound is used as a starting material compound.

(Kit)

Two or more of the same compounds which are the aforementioned isotope labeling compounds of the present invention except that the mass number is different due to isotope labeling are combined to give a kit using a mass spectrometer for quantification of an amino group-containing target substance in a biological sample (hereinafter to be also referred to as the kit of the present invention). The target substance may be any compound as long as it contains an amino group, which is typically an amino group-containing non-peptidic compound (e.g., amine, amino acid etc.), an amino group-containing peptide compound or a protein.

The combination of the isotope labeling compounds of the present invention to be contained in the kit of the present invention is not particularly limited.

When the target substance is a protein, a combination that achieves a mass difference of not less than 6 between any compounds is preferable since it can avoid interference between isotope peaks in mass spectrum. Examples of such combination include one including a compound represented by the formula (I), which does not contain a carbon atom having a mass number of 13, a compound represented by the formula (I), which has 6 carbon atoms having a mass number of 13, and a compound represented by the formula (I), which has 12 carbon atoms having a mass number of 13, or a salt thereof. Specific examples of preferable combination include one including the above-mentioned PyII-0, PyII-6 and PyII-12.

When the target substance is an amino group-containing non-peptidic compound, interference between isotope peaks can be avoided between any compounds as long as the mass difference is two or more. As such combination, therefore, one including two or more compounds represented by the formula (I) and having a mass difference of two or more or a salt thereof can be mentioned. Examples of such combination include those containing two or more compounds selected from the group consisting of a compound represented by the formula (I), which does not contain a carbon atom having a mass number of 13, a compound represented by the formula (I), which has 2 carbon atoms having a mass number of 13, a compound represented by the formula (I), which has 4 carbon atoms having a mass number of 13, a compound represented by the formula (I), which has 6 carbon atoms having a mass number of 13, a compound represented by the formula (I), which has 8 carbon atoms having a mass number of 13, a compound represented by the formula (I), which has 10 carbon atoms having a mass number of 13, and a compound represented by the formula (I), which has 12 carbon atoms having a mass number of 13, or a salt thereof. Specific examples of preferable combination include those containing two or more from the above-mentioned PyII-0, PyII-2, PyII-4, PyII-6, PyII-8, PyII-10 and PyII-12. In addition, since more samples can be collectively treated, each combination exemplified above preferably contains 3 or more, more preferably 4 or more, further preferably 5 or more, particularly preferably 6 or more, most preferably 7, compounds represented by the formula (I) or a salt thereof.

The kit of the present invention may contain, besides the combination of the isotope labeling compounds of the present invention, one or more reaction buffers, washing solutions, or other components necessary or preferable for use in combination with the isotope labeling compound of the present invention. In addition, the kit of the present invention optionally contains an instruction manual thereof. Furthermore, the kit of the present invention may further contain a reagent for removing an unreacted component (washing reagent), a restriction enzyme, a column for purification, a solvent for purification and the like.

(Quantitative Analysis Method)

The present invention also provides a method of quantitatively analyzing an amino group-containing target substance in two or more biological samples by using a mass spectrometer, which utilizes two or more isotope labeling compounds of the present invention mentioned above (hereinafter to be also referred to as the quantitative analysis method of the present invention). As the target substance, an amino group-containing non-peptidic compound, an amino group-containing peptide compound, a protein and the like can be mentioned. The quantitative analysis method of the present invention can be essentially performed according to similar steps, irrespective of the kind of the target substance. However, a quantitative analysis method of protein (hereinafter to be also referred to as the protein analysis method of the present invention) is separately explained later, since special treatments such as digestion with a restriction enzyme, identification of protein from peptide fragment and the like are generally performed. In addition, quantitative analysis of a peptide compound wherein the number of amino acids is generally 2 to about just over a dozen pieces is not particularly explained since those of ordinary skill in the art can appropriately perform same based on the explanation of the analysis method of the below-mentioned protein. The quantitative analysis method of the amino group-containing non-peptidic compound (hereinafter to be also referred to as the non-peptidic compound analysis method of the present invention) is explained below.

(Quantitative Analysis Method of Amino Group-Containing Non-Peptidic Compound)

In the present specification, the amino group-containing non-peptidic compound or the non-peptidic compound having an amino group means any compound having one or more amino groups in a molecule, and free of a peptide bond in a molecule. Here, the amino group means a monovalent functional group obtained by removing a hydrogen from ammonia, primary amine (i.e., compound wherein one hydrogen atom of ammonia is substituted by any optionally substituted hydrocarbon group) or secondary amine (i.e., compound wherein two hydrogen atoms of ammonia are substituted by the same or different, any optionally substituted hydrocarbon groups). Thus, the amino group-containing non-peptidic compound is a non-peptidic compound having a chemical formula of $NH_3$, $NH_2R$, or $NHRR'$ wherein R and R' are the same or different and each is any optionally substituted hydrocarbon group. However, a compound having a chemical formula of $NHRR'$ is considered to be unreactive or extremely low-reactive with the labeling reagent used in the method of the present invention. Therefore, the amino group-containing non-peptidic compound to be the target of the method of the present invention is generally a non-peptidic compound having a chemical formula of $NH_2R$ wherein R is hydrogen or any optionally substituted hydrocarbon group.

While the molecular weight of the amino group-containing non-peptidic compound to be the measurement target is not particularly limited as long as the method of the present invention can be performed, it is generally a low molecular weight compound. A specific molecular weight is 17-1000, preferably 17-700, more preferably 17-500. Examples of the amino group-containing non-peptidic compound to be measured include biologically active amines, amino acids, drugs, stimulant drugs, narcotics, involatile putrefactive amines, and metabolites thereof having an amino group and the like. It is also possible to measure plural kinds of amino group-containing non-peptidic compounds by a single analysis.

More specific examples of the amino group-containing non-peptidic compound include, but are not limited to, biologically active amines that act on the nerve system (e.g., L-DOPA, norepinephrine (noradrenalin), dopamine, tryptamine, serotonin, ptomaine, histamine, tyramine, taurine etc.), various biological amino acids (e.g., arginine, asparagine, aspartic acid, cysteine, glutamine, glutamic acid, glycine, histidine, isoleucine, leucine, lysine, methionine, phenylalanine, serine, threonine, tryptophan, tyrosine, valine, γ-aminobutyric acid (GABA), and modified products thereof (e.g., phosphorylated product etc.) etc.), drugs and narcotics (e.g., phenethylamine, amphetamine, cathine, cathinone, phentermine, mescaline, MDA, methoxyamphetamine, BDB, HMA, 2C-B, DOB, DOM, DOET, MMDA, TMA, 2C-I, 2C-D, 2C-N, 2C-T-2, 2C-T-7, DOI, DON, 2,5-DMA, 3,4-DMA etc.), involatile putrefactive amines (e.g., spermidine, spermine, putrescine, cadaverine etc.), as well as metabolites thereof having an amino group and the like.

Each step is explained below.

(1) Step of Preparing Two or More Biological Samples to be Subjected to Analysis The number of biological samples to be subjected to analysis is not particularly limited. When more samples than the number of the kind of the isotope labeling compounds of the present invention mutually having a mass difference (e.g., 7 isotope labeling compounds mutually having a mass difference of 2) are to be analyzed, the samples are divided into two or more groups, and each group is analyzed also using the internal standard sample. The internal standard sample is described below.

As a biological sample to be subjected to the analysis, one obtained from any derivation and tissues and the like according to the object of analysis by a method known per se can be utilized. Specifically, examples of the biological sample include, but are not limited to, samples containing various body fluids (e.g., blood, bone marrow fluid, cerebrospinal fluid, saliva, lacrimal fluid, gastric fluid, ascites, exudate, amniotic membrane fluid, pancreatic juice, bile and the like), excretions (e.g., urine, stool and the like), and cells and tissues (e.g., brain, spinal cord, eyeball, stomach, pancreas, kidney, liver, gonad, thyroid gland, gall bladder, bone marrow, adrenal gland, skin, lung, digestive tract (e.g., large intestine, small intestine), blood vessel, heart, thymus, spleen, submandibular gland, peripheral blood, prostate, orchis, ovary, placenta, uterus, bone, articular, adipose tissue, skeletal muscle and the like) and the like of mammals (e.g., human, monkey, bovine, horse, swine, sheep, goat, dog, cat, rabbit, hamster, guinea pig, mouse, rat etc.). From the obtained sample, the target non-peptidic compound is preferably concentrated in each biological sample by a suitable means such as solid phase extraction and the like. The concentration can be performed by, for example, the following procedures. That is, in each harvested sample, the target non-peptidic compound and proteins are separated by a deproteinization treatment using a suitable means such as acid extraction and the like. Then, the target non-peptidic compound in the deproteinized liquid sample is trapped by a cation exchange resin capable of selectively trapping same. Then, an acidic or neutral low molecular substance that non-specifically adsorbed to the resin is washed with alcohol. The residual resin-bound cation is eluted with hydrochloric acid and the like and thereafter hydrochloric acid is removed under reduced pressure. As a result, a biological sample to be subjected to analysis can be prepared.

In this step, it is preferable to prepare the internal standard sample as one of the samples to be subjected to analysis. The internal standard sample is a sample to be the standard of the amount of the target non-peptidic compound contained in a sample. Comparison among plural samples can be performed with higher accuracy by determining the amount of a target non-peptidic compound contained in plural samples to be analyzed as a relative value to the amount of the compound contained in the internal standard sample, and comparing the values. Even when the number of the samples to be analyzed is higher than the number of the kind of the isotope labeling compounds of the present invention mutually having a mass difference, which can be prepared for labeling, the samples to be analyzed are divided into two or more groups, and each group is analyzed using the same internal standard sample, whereby all samples to be analyzed can be compared.

An internal standard sample can be prepared by, for example, dissolving a commercially available product of a target non-peptidic compound in a given concentration (e.g., 0.05M) HCl. While the concentration of the target non-peptidic compound in the internal standard sample is not particularly limited, it is generally preferably near the assumed concentration of the compound in a sample to be subjected to analysis. An internal standard sample generally contains a target non-peptidic compound at a known concentration. In this way, an absolute amount of the target compound present in a sample can be determined.

After this step and before step (2), to determine the mixing ratio between samples in the later step (3), a non-peptidic compound containing an amino group not present in any sample to be subjected to the analysis may be added to all samples to a known concentration as a compound to be an index of the mixing ratio. Examples of the compound to be an index of the mixing ratio include dihydroxybenzylamine (DHBA) and the like. While the amount to be added of the compound indicative of mixing ratio is not particularly limited as long as the mass spectrometry is not adversely affected, it is added such that, for example, the concentration of the compound indicative of mixing ratio in each sample is 0.2-10 pmol, preferably 0.5-5 pmol, more preferably 1-3 pmol. Preferably, the compound indicative of mixing ratio is added such that the concentration thereof is same in samples to be subjected to analysis.

(2) Step of Labeling a Target Substance in Samples Prepared by Using, as a Labeling Compound, Two or More Compounds Having a Mutually Different Mass Due to Isotope Labeling, which are Represented by the Formula (I) or a Salt Thereof, to Confer a Mass Difference to the Target Substance Between the Samples In this step, each sample prepared in step (1), a target amino group-containing non-peptidic compound is labeled using a different isotope labeling compound of the present invention. The amino group-containing non-peptidic compound shows basicity and has a comparatively high pKa value. When the pH of the reaction mixture is lower than the pKa value thereof, the amino group takes the ion type of —$NH_3^+$. When the pH of the reaction mixture is higher by 2 pH units than the pKa value thereof, $H^+$ is released to take the structure of —$NH_2$. It is known that the isotope labeling compound of the present invention shows higher reactivity to —$NH_2$. Therefore, the pH of the reaction mixture can be appropriately adjusted according to the pKa value of the target non-peptidic compound. When amino group-containing non-peptidic compounds in samples are simultaneously quantified, since the range of pKa of amino group-containing non-peptidic compound is wide, the maximum pH of 10.0 may be employed as a pH range that can be protected with borate buffer. Specific composition of the reaction mixture is, for example, as described below: 0.05 M borate buffer (pH 10.0, 10 μL), 0.05 M hydrochloric acid solution (10 mM, 1 μL) of amino group-containing non-peptidic compound, distilled water, 100 mM PyII compound (1 μL), the total amount 20 μL. The reaction is performed at, for example, 50° C. for several min to 2 hr, and the reaction is stopped by adding 1M hydrochloric acid (1 μL).

As the combination of the labeling compounds to be used, one including two or more compounds represented by the formula (I) and having a mass difference of two or more or a salt thereof can be mentioned. Examples of such combination include those containing two or more compounds selected from the group consisting of a compound represented by the formula (I), which does not contain a carbon atom having a mass number of 13, a compound represented by the formula (I), which has 2 carbon atoms having a mass number of 13, a compound represented by the formula (I), which has 4 carbon atoms having a mass number of 13, a compound represented by the formula (I), which has 6 carbon atoms having a mass number of 13, a compound represented by the formula (I), which has 8 carbon atoms having a mass number of 13, a compound represented by the formula (I), which has 10 carbon atoms having a mass number of 13, and a compound represented by the formula (I), which has 12 carbon atoms having a mass number of 13, or a salt thereof. Specific examples of preferable combination include one including two or more of the above-mentioned PyII-0, PyII-2, PyII-4, PyII-6, PyII-8, PyII-10 and PyII-12. In addition, since more samples can be collectively treated, each combination exemplified above preferably contains 3 or more, more preferably 4 or more, further preferably 5 or more, particularly preferably 6 or more, most preferably 7, compounds represented by the formula (I) or a salt thereof.

The isotope-labeled compound of the present invention labels an amino group-containing non-peptidic compound according to the following reaction formulas:

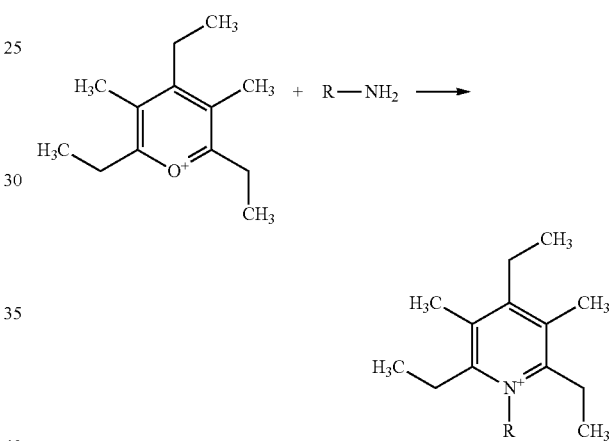

The same target non-peptidic compound derived from different samples is labeled with a compound having a different mass due to isotope labeling and, as a result, has a mutually different mass.

(3) Step of Preparing a Mixture from all Samples Subjected to the Labeling

In this step, each amino group-containing non-peptidic compound-containing samples subjected to the labeling in step (2) are mixed. The amount taken from each sample for the preparation of the mixture is preferably equal, but is not limited thereto. An excess labeling reagent present in the mixture may be removed, though the removal is not always necessary. An excess labeling reagent can be removed by organic solvent extraction using ethyl acetate and the like, or by using a cation exchange resin. Furthermore, the mixture is preferably concentrated before mass spectrometry. For concentration of the mixture, the mixture is added to an equilibrated cation exchange resin ($H^+$-type), washed well with water, and the reaction product is eluted with 1% aqueous ammonia or 0.1M hydrochloric acid. The elution is performed by concentration to a suitable amount by a reduced pressure centrifugal concentrator.

(4) Step of Subjecting the Mixture to Mass Spectrometry, Determining a Presence Ratio of the Target Substance in the Mixture Based on the Ratio of Peak Intensity in Mass Spectrum of a Target Substance Mutually Having a Mass Difference Due to Labeling, and Determining a Quantitative Ratio of the Target Substance Between Samples Subjected to the Preparation of the Mixture, from the Obtained Presence Ratio and the Mixing Ratio of the Samples in Step (3)

In this step, the mixture obtained according to the above-mentioned procedures is subjected to mass spectrometry. Mass spectrometry can be performed according to a known method. While the quantitative method of the present invention permits use of any mass spectrometry system, analysis using a nano-liquid chromatographic mass spectrometry (nano-LC/MS) system (e.g., NanoFrontier eLD (manufactured by Hitachi High-Technologies Corporation) and the like) is preferable since it enables high sensitive quantification. In addition, mass spectrometry according to a conventional method affords mass spectrum. Specifically, for example, it can be performed as follows:

LC conditions are: using monolith-type MonoCap for Fast-Flow (0.075 mm ID×150 mmL, GL Sciences Inc.) as a separation column, and C18-Monolith trap column (0.05 mm ID×150 mm L GL Sciences Inc.) as a trap column, gradient elution is performed at flow 200 nl/min, mobile phase A) formic acid/water/acetonitrile (0.1:98:2), B) formic acid/water/acetonitrile (0.1:2:98) (i.e., A/B=98/2 (0 min)-2/98 (50 min)-2/98 (50.1-70 min)-98/2 (70.1-90 min)). Mass measurement section settings: ionization mode nano-ESI (positive ionization), spray voltage 1600 V, detector voltage 1950 V, counter nitrogen gas rate 0.8 L/min, scan range 100-500 m/z. The mass spectrometry recording time is 50 min.

Due to the isotope labeling, the same kind of amino group-containing non-peptidic compounds derived from different samples have different mass. Therefore, in the mass spectrum, the amino group-containing non-peptidic compounds derived from different samples appear as separated peaks. By determining the intensity ratio of the separated peaks, the presence ratio of the peptides in the aforementioned mixture can be obtained.

When the internal standard sample is also subjected to the analysis, the presence ratio in this step is generally determined by obtaining the peak intensity ratio of the target non-peptidic compound derived from each sample other than the internal standard sample and the same compound derived from the internal standard sample and different only in the mass.

When a compound to be an index of the mixing ratio is added for the analysis, the peak intensity ratio in mass spectrum of a compound to be an index of the mixing ratio and mutually having a mass difference due to the labeling in step (2) is determined in this step. The determined ratio corresponds to the presence ratio of the compound in the aforementioned mixture. Thus, the mixing ratio between samples in step (3) can be determined from the concentration of the compound to be an index of the mixing ratio and added to each sample, and the presence ratio of the compound to be an index of the determined mixing ratio in the aforementioned mixture.

The quantitative ratio of the target non-peptidic compound among samples subjected to the preparation of the mixture can be determined from the presence ratio obtained as mentioned above and the mixing ratio of the samples in step (3).

(Method of Quantitative Analysis of Protein)

Each step of the protein analysis method of the present invention is explained below.

(1) Step of Preparing Two or More Biological Samples to be Subjected to an Analysis The number, derivation and collection method of the sample subjected to the analysis are as described above for the non-peptidic compound analysis method of the present invention. It is preferable to perform an extraction treatment of protein from the collected samples by a method known per se. Specifically, for example, an extraction treatment of protein can be performed by using a solution called a cell lysate solution (CLS; cell lysate solution). The composition of CLS is 7M urea, 3M thiourea, 2% CHAPS, 0.2M borate buffer, pH 9.6. To improve accuracy of analysis, it is also preferable to prepare a sample having the same total protein amount as that of each sample obtained by an extraction treatment from each sample and use a sample thus produced for the subsequent analyses.

In this step, it is preferable to prepare the internal standard sample as one of the samples to be subjected to analysis. The internal standard sample is a sample to be the standard of the amount of each protein contained in a sample. Comparison among plural samples can be performed with higher accuracy by determining the amount of the given protein contained in plural samples to be analyzed as a relative value to the amount of the protein contained in the internal standard sample, and comparing the values. Even when the number of the samples to be analyzed is higher than the number of the kind of the isotope labeling compounds (e.g., 3 isotope labeling compounds having mutual mass difference of 6) of the present invention mutually having a mass difference, which can be prepared for labeling, the samples to be analyzed are divided into two or more groups, and each group is analyzed using the same internal standard sample, whereby all samples to be analyzed can be compared.

For the above-mentioned object, the internal standard sample preferably contains any protein present in the samples to be analyzed. For this end, the internal standard sample may be prepared by, for example, mixing all protein-containing samples to be analyzed, which are prepared as mentioned above. In this case, one example of the preparation method thereof include preparing starting samples having the same total protein content from each sample prepared as mentioned above, and mixing the starting samples (e.g., mixing of equal amounts) to give an internal standard sample.

A quantitative analysis method of protein using the internal standard sample is also explained in the above-mentioned patent document 1.

(2) Step of Labeling a Protein in Samples Prepared by Using, as a Labeling Compound, Two or More Compounds Having a Mutually Different Mass Due to Isotope Labeling, which are Represented by the Formula (I) or a Salt Thereof, to Confer a Mass Difference to the Same Protein Between the Samples In this step, protein is labeled by using a different isotope labeling compound of the present invention for each sample prepared in step (1). For this end, the SH group of the total protein in a sample to be subjected to the analysis is generally applied to reduction and alkylation treatments before labeling. Such treatments can be performed according to conventional methods and, for example, dithiothreitol can be used for reduction and iodoacetamide can be used for alkylation. A labeling reaction can be performed by adding, under basic conditions, the labeling compound to a protein containing sample dissolved in a suitable solvent (e.g., the above-mentioned CLS; the reaction mixture is prepared such that the final concentration after addition of the labeling compound is urea 6.5M, thiourea 2.5M, CHAPS not less than 1.7%), and reacting the mixture at 50° C. for 2 hr. The amount of the labeling compound can be a 100-fold amount of the lysine residue in the protein present in the sample.

As the combination of the labeling compounds to be used, one showing a mass difference of not less than 6 in any compounds is preferable. Examples of such combination include those containing two or more compounds selected from the group consisting of a compound represented by the formula (I), which does not contain a carbon atom having a mass number of 13, a compound represented by the formula (I), which has 6 carbon atoms having a mass number of 13, and a compound represented by the formula (I), which has 12 carbon atoms having a mass number of 13, or a salt thereof. Specific examples of preferable combination include those containing the above-mentioned PyII-0, PyII-6 and PyII-12.

The isotope labeling compound of the present invention is bound to a ε-amino group of the lysine residue of a protein according to the following reaction formulas:

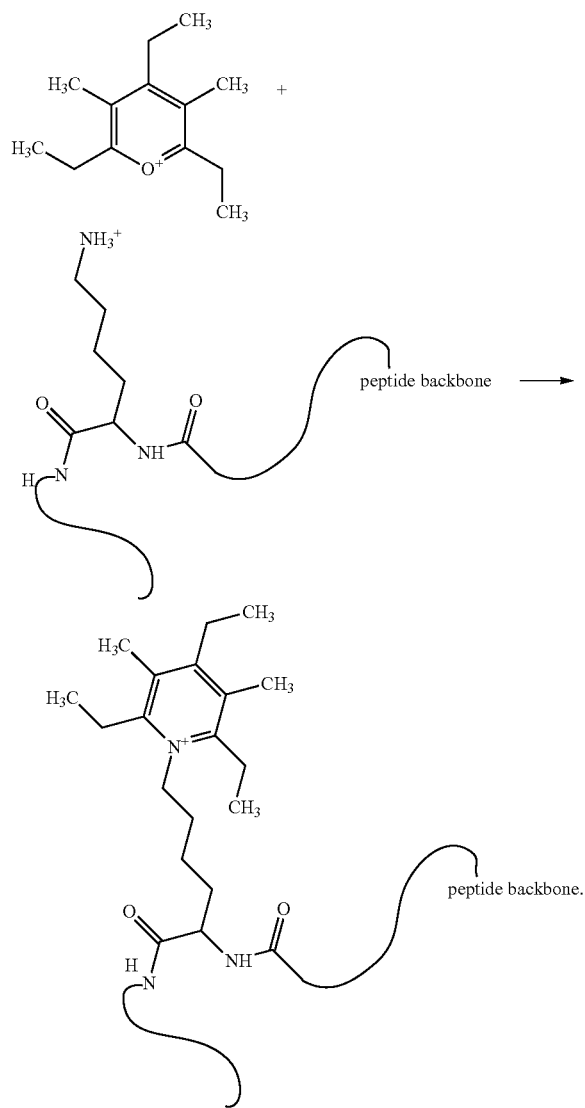

It rarely reacts with the α-amino group. The same protein derived from different samples is labeled with a compound having a different mass due to isotope labeling and, as a result, has a mutually different mass.

(3) Step of Preparing a Mixture from all Samples Subjected to the Labeling

In this step, respective protein-containing samples labeled in step (2) are mixed. For example, it is preferable to mix in equal amounts so that the protein amount from each sample will be the same. Unreacted labeling compounds are generally removed by gel filtration method or protein precipitation reagent, and labeled proteins are collected and concentrated.

(4) Step of Digesting the Protein in the Mixture with a Protease to Give a Peptide This step largely follows either of the following two methods:

(a) the mixture is roughly separated by one-dimensional gel separation, two-dimensional gel separation or suitable chromatomedia and the like, and the resulting protein is hydrolyzed with protease to liberate peptides; and (b) the mixture is directly degraded with protease, without previously subjecting the contained protein to gel separation or development by chromatography for separation from each other as in (a).

Protein degradation can be performed according to the procedures known per se. Besides trypsin of the primary selection, Arg peptidase, Glu peptidase and the like are used as the secondary selection; however, Lys endopeptidase is not used.

The flow after liberation of peptides to mass spectrometry of peptides is as follows.

The labeled peptides and unlabeled peptides liberated from the protein separated by the operation in (a) may sometimes be directly subjected to mass spectrometry by MALDI-TOF/MS, without a peptide separation operation. It is also possible to separate peptides by liquid chromatography and subject the peptide to ESI/MS/MS analysis.

The peptides liberated by the operation in (b) is separated by a two-dimensional liquid chromatograph system such as one wherein one-dimensional separation is performed with an SCX column, and the eluted components are separated using a second reversed-phase resin column, and introduced into ESI/MS/MS, whereby relative intensity of the labeled peptide and the amino acid sequence information thereof are obtained by a single analysis.

Here, while the molecular weight of the peptides to be used for the measurement of MS spectrum in the next step is not particularly limited, the molecular weight is for example, 500-3000, preferably 1000-2500. Therefore, this step preferably includes isolation of peptide having a molecular weight in the above-mentioned range from protease digestion products.

(5) Step of Subjecting the Obtained Peptide to Mass Spectrometry, and Determining a Presence Ratio of the Peptide in the Mixture Based on the Ratio of Peak Intensity in Mass Spectrum of the Peptide Mutually Having a Mass Difference Due to Labeling In this step, the peptide obtained according to the above-mentioned procedures is subjected to mass spectrometry. While the present invention permits use of any mass spectrometry system, analysis using a nano-liquid chromatographic mass spectrometry (nano-LC/MS) system (e.g., NanoFrontier eLD (manufactured by Hitachi High-Technologies Corporation) and the like) is preferable since it enables high sensitive quantification. Mass spectrum can be obtained by conducting mass spectrometry according to a conventional method.

Due to the isotope labeling, the same kind of peptides derived from different samples have different mass. Therefore, in the mass spectrum, the peptides derived from different samples appear as separated peaks. The presence ratio of the peptide in the aforementioned mixture can be obtained by determining the intensity ratio of the separated peaks.

Although generally not necessary when a labeling compound having a mass difference of not less than 6 is used for labeling in step (2), otherwise, the quantitative ratio is corrected by removing the overlap with the isotope peak of peptide due to naturally occurring isotope for comparison of the peak intensity, as taught in, for example, JP-A-2005-181011.

When the internal standard sample is also subjected to the analysis, the presence ratio in this step is generally determined by obtaining the peak intensity ratio of the peptide derived from each sample other than the internal standard sample and the same peptide derived from the internal standard sample and different only in the mass.

(6) Step of Identifying a Protein from which the Peptide Having the Determined Presence Ratio Derives, and Determining a Quantitative Ratio of the Protein Between Samples Subjected to the Preparation of the Mixture, from the Presence Ratio and the Mixing Ratio of the Samples in Step (3)

In this step, the protein from which the peptide derives can be specified by referring to the mass spectrum in step (5), a peptide whose amino acid sequence is to be determined, and assessing the amino acid sequence of the peptide based on the MS/MS spectrum of the product ion generated from the peptide; and from known DNA sequences, the corresponding protein based on the amino acid sequence of the peptide.

Here, since the presence ratio of the peptide obtained in step (5) is equal to the presence ratio of the protein, from which the peptide derives, in the aforementioned mixture, the quantitative ratio of the protein among samples subjected to the preparation of the mixture can be determined from the presence ratio and the mixing ratio of the samples in step (3).

(Labeling Compound)

The present invention further provides a compound represented by the formula (IV):

(IV)

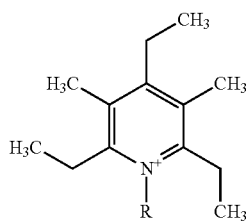

wherein R is any optionally substituted hydrocarbon group (excluding a compound having a peptide bond), or a salt thereof. The compound or a salt thereof may have one or more (e.g., 1, 2, 3, 4, 5, 6, 7, 8, 9, 10, 11, 12, 13) carbon atoms having a mass number of 13 at a position other than R in the formula (IV). Hereinafter, a compound represented by the formula (IV) or a salt thereof, including those not labeled with an isotope, is also referred to as the labeled product of the present invention. The labeled product of the present invention can be utilized, for example, for the preparation of an internal standard sample in the non-peptidic compound analysis method of the present invention, and the like.

The labeled product of the present invention may be produced, for example, by labeling an amino group-containing non-peptidic compound defined above with the isotope labeling compound of the present invention. That is, any compound obtained by labeling the amino group-containing non-peptidic compound defined above with said labeling compound is encompassed in the labeled product of the present invention. In this case, the position of $^{13}C$ in the labeled product of the present invention corresponds to the position of $^{13}C$ in the isotope labeling compound of the present invention.

Therefore, R in the formula (IV) may be the same as R in any amino group-containing non-peptidic compound having a chemical formula of $NH_2R$ wherein R is hydrogen or any optionally substituted hydrocarbon group, which is described above for the non-peptidic compound analysis method of the present invention. The salt may be any salt, and examples thereof include those exemplified as the salts of the compound of the formula (I) (e.g., trifluoromethanesulfonate, hexafluorophosphate, tetrafluoroborate, perchlorate, trimethylsilyl trifluoromethanesulfonate, methanesulfonate etc.), and nitrate salt, hydrochloride, sulfate and the like.

EXAMPLES

The present invention is explained in detail in the following by referring to Examples and the like, which are not to be construed as limitative.

(1) Analysis Method

Identification of the compound and calculation of deuteration rate were performed by measuring NMR or MS.

(2-1) Apparatus

NMR Analysis

Fourier-transform nuclear magnetic resonance (NMR) apparatus manufactured by JEOL Ltd.

JNM-ECS400

Chemical Purity Analysis high performance liquid chromatography (HPLC) apparatus manufactured by GL Sciences Inc.

GL-7400 series

EI-MS Analysis electron impact mass spectrometry (EI-MS) apparatus manufactured by JEOL Ltd.

JMS-AX505W (2-2) Identification

Identification of Compound by GC-MS Measurement

GC-MS was measured for an undeuterated sample and a $^{13}C$-labeled reagent, and whether the data in support of changes in the molecular weight due to $^{13}C$ labeling were obtained was confirmed.

Identification of Compound by NMR Measurement

Sample was dissolved in $D_2O$, and confirmed from the observed peak information. A $^{13}C$ labeling site can be confirmed by large coupling of proton adjacent to $^{13}C$-labeled carbon.

(2-3) Calculation Method of $^{13}C$ Concentration Rate

GC-MS was measured for an undeuterated sample and a $^{13}C$-labeled reagent under the same conditions, and the rate was calculated from the peak intensity ratio of the obtained fragment.

(2-4) Chemical Purity Analysis

HPLC analysis was performed, and the chemical purity was calculated from the obtained peak area ratio.

(3) Reagent manufactured by Tokyo Chemical Industry Co., Ltd.: general reagent manufactured by TAIYO NIPPON SANSO CORPORATION or manufactured by ISOTEC Corporation: $^{13}C$ label starting material Example 1

2,4,6-Triethyl-3,5-dimethylpyrylium trifluoromethanesulfonate (PyII-0)

3-Ethyl-2-pentanol (136 µl, 116 mg, 1 mmol) and anhydrous propionic acid (514 µl, 520 mg, 4 mmol) were added into a 10 ml flask, and trifluoromethanesulfonic acid (180 µl, 222 mg, 1 mmol) was added dropwise while stirring at room temperature. After completion of dropwise addition, the mixture was heated to 65° C. and reacted for 1.5 hr. Thereafter, the reaction mixture was concentrated under reduced pressure, neutralized, and extracted by partitioning with an organic solvent. The extracted organic solvent was dehydrated over magnesium sulfate, concentrated and recrystallized to give 2,4,6-triethyl-3,5-dimethylpyrylium trifluoromethanesulfonate (PyII-0) (176 mg, 0.49 mmol, yield 52%).

chemical purity: 99.6%

$^1$H-NMR (270 MHz, $D_2O$): δ:1.06 (3H, t, J=7.7 Hz), 1.27 (6H, t, J=7.4 Hz), 2.30 (6H, s), 2.85 (2H, q, J=7.7 Hz), 3.07 (4H, q, J=7.5 Hz)

EI-MS: m/z for $C_{13}H_{21}O^+$ (M-$CF_3SO_3$) calculated 193.16. found 193.2.

Example 2

2,4,6-Triethyl-3,5-dimethylpyrylium 2,6-$^{13}C_2$ trifluoromethanesulfonate (PyII-2)

By an operation similar to that in Example 1 except that a $^{13}$C-labeled compound was used as the starting material, 2,4,6-triethyl-3,5-dimethylpyrylium 2,6-$^{13}C_2$ trifluoromethanesulfonate (PyII-2) was synthesized.

chemical purity: 99.6%

$^{13}$C enrichment: 99.3 atom % $^{13}$C $^1$H-NMR (270 MHz, $D_2O$): δ:1.07 (3H, t, J=7.7 Hz), 1.28 (6H, td, J=7.4 Hz, 5.1 Hz), 2.31 (6H, d, J=5.3 Hz), 2.81 (2H, q, J=7.7 Hz), 3.08 (4H, dt, J=14.2 Hz, 6.3 Hz)

EI-MS: m/z for $^{13}C_2C_{11}H_{21}O^+$ (M-$CF_3SO_3$) calculated 195.29. found 195.2.

Example 3

2,4,6-Triethyl(4-$^{13}C_1$)-3,5-dimethyl-$^{13}C_2$-pyrylium 4-$^{13}C_1$ trifluoromethanesulfonate (PyII-4)

By an operation similar to that in Example 1 except that a $^{13}$C-labeled compound was used as the starting material, 2,4,6-triethyl(4-$^{13}C_1$)-3,5-dimethyl-$^{13}C_2$-pyrylium 4-$^{13}C_1$ trifluoromethanesulfonate (PyII-4) was synthesized.

chemical purity: 99.9%

$^{13}$C enrichment: 99.1 atom % $^{13}$C $^1$H-NMR (270 MHz, $D_2O$): δ:1.06 (3H, ddd, J=127.8 Hz), 1.28 (6H, t, J=7.3 Hz), 2.31 (6H, dd, J=129.8 Hz, 3.7 Hz), 2.86 (2H, dt, J=19.9 Hz, 6.8 Hz), 3.08 (4H, q, J=7.4 Hz)

EI-MS: m/z for $^{13}C_4C_9H_{21}O^+$ (M-$CF_3SO_3$) calculated 197.28. found 197.2.

Example 4

2,4,6-Triethyl(4-$^{13}C_2$)-3,5-dimethyl-$^{13}C_2$-pyrylium 3,5-$^{13}C_2$ trifluoromethanesulfonate (PyII-6)

By an operation similar to that in Example 1 except that a $^{13}$C-labeled compound was used as the starting material, 2,4,6-triethyl(4-$^{13}C_2$)-3,5-dimethyl-$^{13}C_2$-pyrylium 3,5$^{13}C_2$ trifluoromethanesulfonate (PyII-6) was synthesized.

chemical purity: 98.8%

$^{13}$C enrichment: 99.5 atom % $^{13}$C $^1$H-NMR (270 MHz, $D_2O$): δ:1.06 (3H, ddt, J=128.5 Hz, 12.8 Hz, 4.7 Hz), 1.27 (6H, t, J=7.4 Hz), 2.30 (6H, dd, 129.6 Hz, 5.9 Hz), 2.85 (2H, dm, J=129.6 Hz), 3.07 (4H, ddd, J=14.8 Hz, 7.3 Hz, 2.2 Hz)

EI-MS: m/z for $^{13}C_6C_7H_{21}O^+$ (M-$CF_3SO_3$) calculated 199.26. found 199.2.

Example 5

2,4,6-Triethyl(4-$^{13}C_2$)-3,5-dimethyl-$^{13}C_2$-pyrylium 2,3,5,6-$^{13}C_4$ trifluoromethanesulfonate (PyII-8)

By an operation similar to that in Example 1 except that a $^{13}$C-labeled compound was used as the starting material, 2,4,6-triethyl(4-$^{13}C_2$)-3,5-dimethyl-$^{13}C_2$-pyrylium 2,3,5,6-$^{13}C_4$ trifluoromethanesulfonate (PyII-8) was synthesized.

chemical purity: 99.8%

$^{13}$C enrichment: 98.4 atom % $^{13}$C $^1$H-NMR (270 MHz, $D_2O$): δ:1.06 (3H, ddd, J=127.8 Hz, 11.4 Hz, 7.3 Hz), 1.27 (6H, dd, J=12.2 Hz, 7.1 Hz), 2.30 (6H, dt, J=129.9 Hz, 5.1 Hz), 2.85 (2H, dm, J=133.4 Hz), 3.07 (4H, t, J=6.3 Hz)

EI-MS: m/z for $^{13}C_8C_5H_{21}O^+$ (M-$CF_3SO_3$) calculated 201.25. found 201.2.

Example 6

2,4,6-Triethyl(2,6-$^{13}C_4$, 4-$^{13}C_1$)-3,5-dimethyl-$^{13}C_2$-pyrylium 2,4,6-$^{13}C_3$ trifluoromethanesulfonate (PyII-10)

By an operation similar to that in Example 1 except that a $^{13}$C-labeled compound was used as the starting material, 2,4,6-triethyl(2,6-$^{13}C_4$,4-$^{13}C_1$)-3,5-dimethyl-$^{13}C_2$-pyrylium 2,4,6-$^{13}C_3$ trifluoromethanesulfonate (PyII-10) was synthesized.

chemical purity: 97.7%

$^{13}$C enrichment: 98.6 atom % $^{13}$C $^1$H-NMR (270 MHz, $D_2O$): δ:1.06 (3H, ddd, J=127.8 Hz, 11.4 Hz, 7.3 Hz), 1.27 (6H, ddt, J=129.9 Hz, 8.9 Hz, 3.3 Hz), 2.30 (6H, dt, J=130.1 Hz, 4.1 Hz), 2.85 (2H, dt, J=133.0 Hz, 7.1 Hz), 3.07 (4H, dm, J=131.0 Hz)

EI-MS: m/z for $^{13}C_{10}C_3H_{21}O^+$ (M-$CF_3SO_3$) calculated 203.23. found 203.2.

Example 7

2,4,6-Triethyl-$^{13}C_6$-3,5-dimethyl-$^{13}C_2$-pyrylium 2,3,5,6-$^{13}C_4$ trifluoromethanesulfonate (PyII-12)

By an operation similar to that in Example 1 except that a $^{13}$C-labeled compound was used as the starting material, 2,4,6-triethyl-$^{13}C_6$-3,5-dimethyl-$^{13}C_2$-pyrylium 2,3,5,6-$^{13}C_4$ trifluoromethanesulfonate (PyII-12) was synthesized.

chemical purity: 99.3%

$^{13}$C enrichment: 99.5 atom % $^{13}$C $^1$H-NMR (270 MHz, $D_2O$): δ:1.06 (3H, dtd, J=129.7 Hz, 7.6 Hz, 4.2 Hz), 1.26 (6H, dtt, J=129.5 Hz, 8.0 Hz, 3.4 Hz), 2.29 (6H, dt, J=129.8 Hz, 5.5 Hz), 2.84 (2H, dm, J=132.2 Hz), 3.06 (4H, dm, J=130.9 Hz)

EI-MS: m/z for $^{13}C_{12}C_1H_{21}O^+$ (M-$CF_3SO_3$) calculated 205.22. found 205.2.

The structural formula of each synthesized PyII compound is shown in the following formula, wherein carbon atoms shown by a black ball has a mass number of 13.

PyII-0 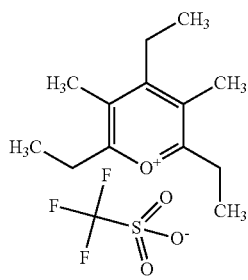

PyII-2 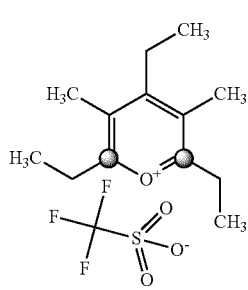

PyII-4 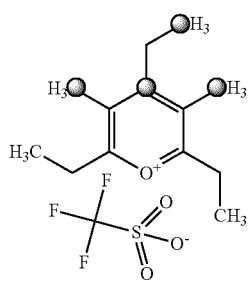

PyII-6 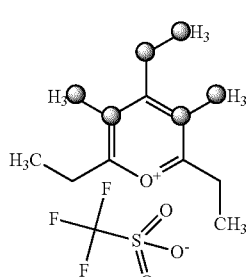

PyII-8 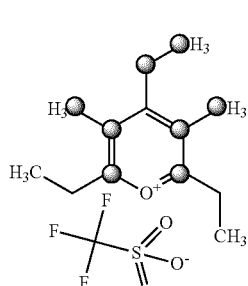

-continued

PyII-10 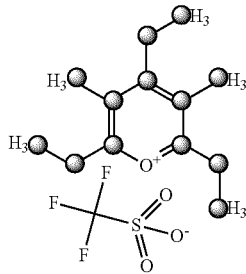

PyII-12 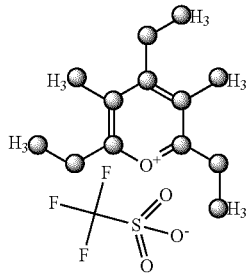

Figure 2:
FIG. 2 shows $^1$H-NMR (270 MHz, $D_2O$) spectrum of each synthesized PyII compound.

FIG. 1 shows EI-MS spectrum of each PyII compound, and FIG. 2 shows $^1$H-NMR (270 MHz, $D_2O$) spectrum of each PyII compound.

Example 8

Evaluation of Effectiveness of PyII Reagent in Proteome Analysis

Whether a PyII reagent is suitable for comprehensive proteome differential expression analysis was studied in the following two experiments.

(1) Confirmation of Operation of PyII Reagent (Mass Difference 6) in Comparison Quantification Method Bovine serum albumin (BSA) and human serum transferrin (Tfn), which are model proteins, were each labeled with PyII-0, PyII-6 and PyII-12, and all samples were mixed at the following mixing ratio.

TABLE 1

| labeling reagent | BSA | Tfn |
|---|---|---|
| PyII-0 | 2 | 8 |
| PyII-6 | 5 | 5 |
| PyII-12 | 8 | 2 |

After mixing, whether the mixing concentration ratio is reflected on a spectrum intensity ratio was studied by comparison quantification.

Figure 3:
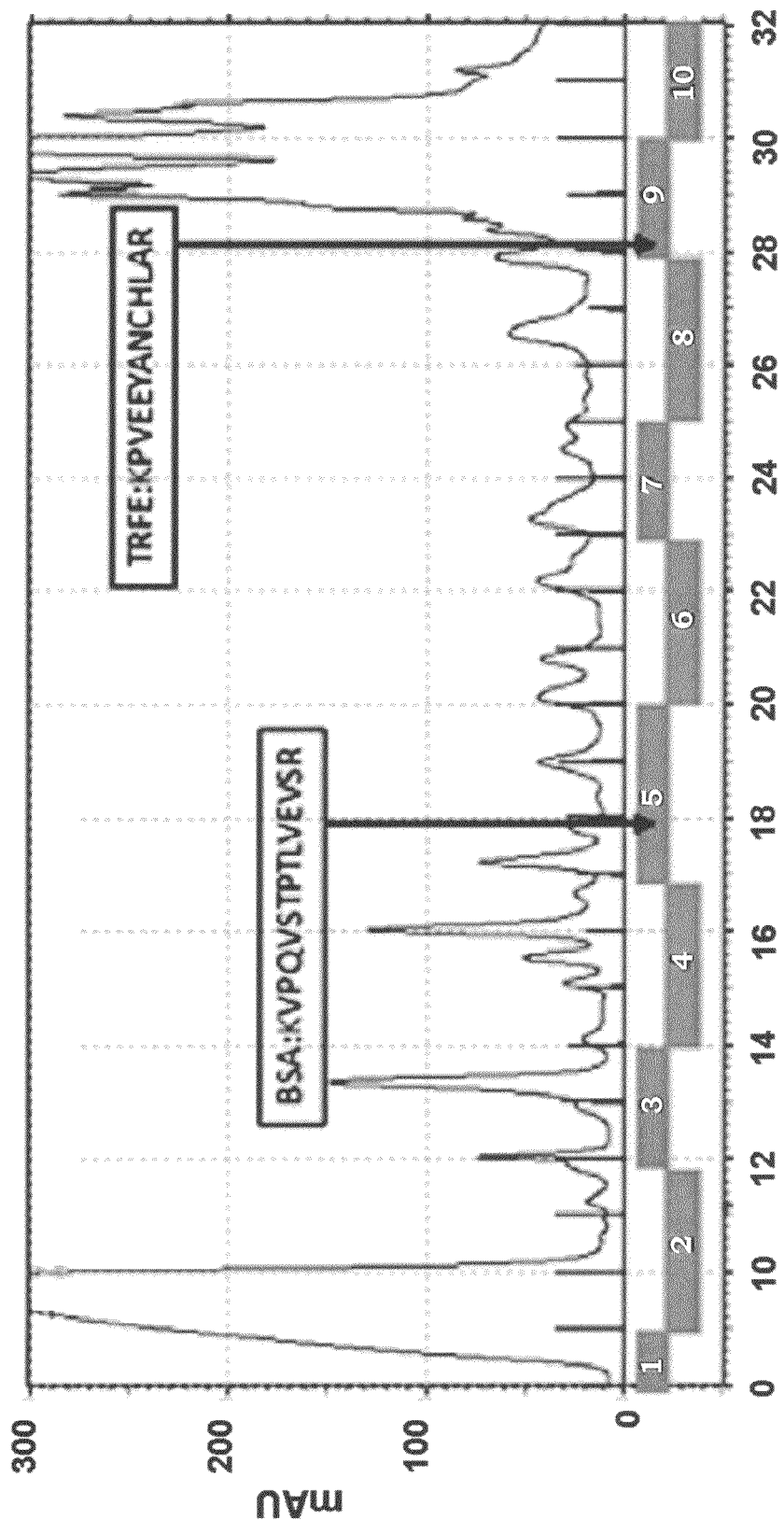
FIG. 3 shows elution curves of bovine serum albumin (BSA)-derived peptide and human serum transferrin (TRFE)-derived peptide.
Figure 4:
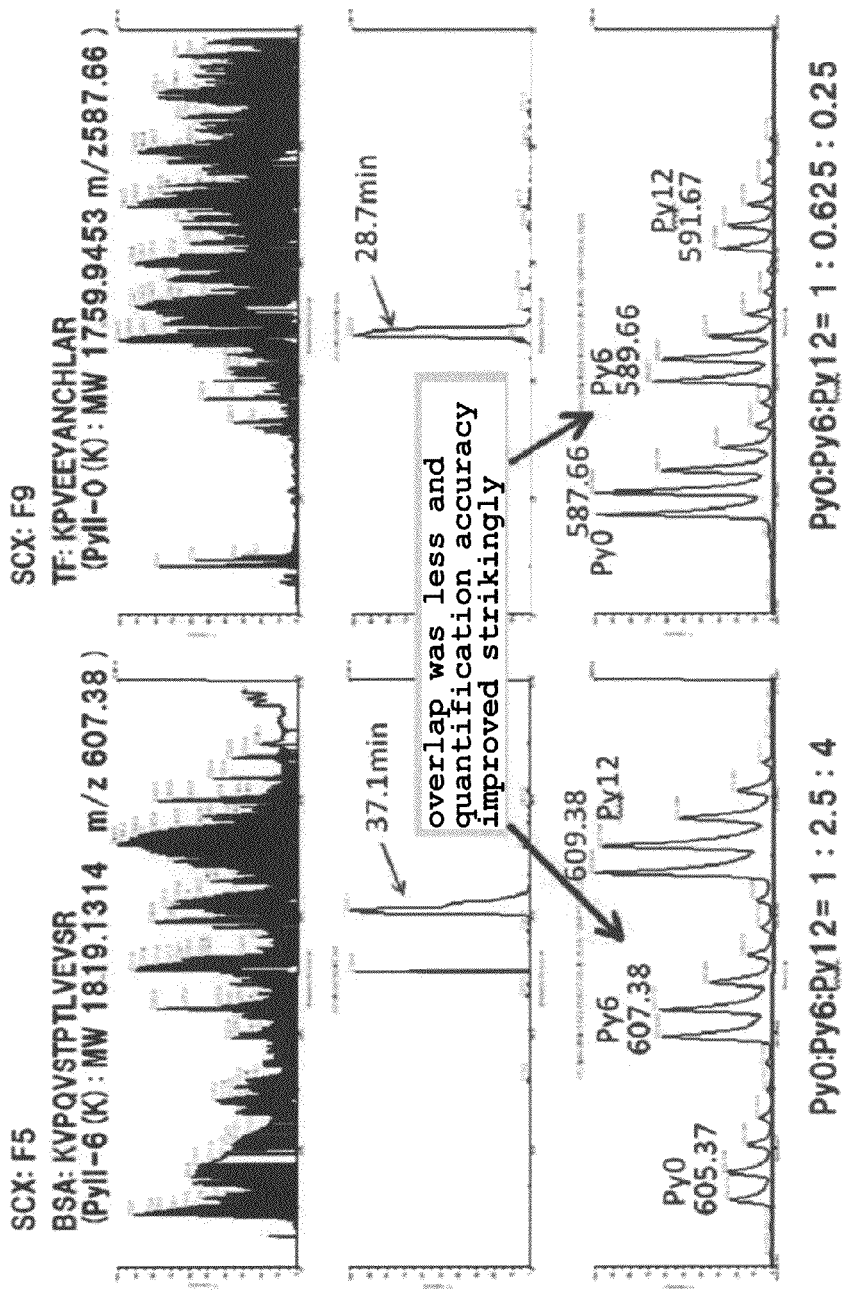
FIG. 4 shows nanoLC/MS/MS analysis results of fraction 5 (including BSA-derived peptide) (left row) and fraction 9 (including TRFE-derived peptide) (eight row) in FIG. 3.

The conditions of SCX fractionation were as follows:
column: Poly Sulfoethyl A 4.6×100 mm
eluent: A=10 mM $KH_2PO_4$ (pH2.8) 25% ACN
B=10 mM $KH_2PO_4$ (pH2.8) 25% ACN 1M KCl
system: HPLC ELITE Lachrom (Hitachi, Ltd.)
sample loop: 2 mL, flow rate: 1 mL/min
Detect: 220 nm, collected at 1 min/tube for 8 min-32 min The elution curves of the BSA-derived peptide and Tfn-derived peptide, which were 10-fractionated by cation exchange (SCX) column, are shown in FIG. 3. BSA-derived peptide and Tfn-derived peptide were detected in fractions 5 and 9. The analysis example of nano LC/MS/MS of the two fractions is shown in FIG. 4. While many peptide-derived ions were detected, a BSA-derived peptide having a molecular weight of 1819.1314 appeared at elution time 37.1 min. The mass spectrometry of this peptide is shown in the lowest panel on the left side in FIG. 4. The peaks of peptides labeled with PyII-0, PyII-6 and PyII-12 in the mass spectrometry appeared at 605.37, 607.38 and 609.38, respectively. This M/z value was exactly one-third of the expected mass, and this peptide was found to be detected as a trivalent ion. This ion gave an intensity ratio of 1:2.5:4. Similarly, Tfn-derived peptide appeared at 28.7 min in fraction 9 since the M/z value was one-third of 1759.9453, and was similarly detected as a trivalent ion. The intensity ratio was 1:0625:0.25. These values were completely the same as the mixing ratio (FIG. 5).

Mass spectrum has a complicated shape including an isotope peak. Monoisotopic peak consists of all elements of peptide, which have the minimum mass, and the first isotope peak is a spectrum of a peptide wherein one carbon is $^{13}C$. In the case of Py reagent having a mass difference of 4, the monoisotopic peak of Py4 overlaps with the 4th isotope peak, and the interference thereof cannot be ignored. However, it was shown that the interference can be completely ignored when the mass difference is 6.

(2) Verification of Comparison Quantification Method with PyII Reagent (Mass Difference 6) in Human Plasma Real Sample Human plasma protein (healthy subject and arteriosclerosis patient) was labeled with PyII reagent. Healthy subject-derived protein was labeled with PyII-0 and PyII-12, arteriosclerosis patient-derived protein was labeled with PyII-6, and they were analyzed according to the protocol shown in FIG. 6. The analysis results of the above-mentioned samples were compared with the cICAT analysis results already performed and the validity of the data was evaluated.

The number of the identified proteins (p<0.05) was 146 and was more than 126 with the cICAT reagent. This may reflect the difference in that PyII is Lys modification and cICAT is Cys modification. The number of the proteins that could be quantified with PyII reagent was 33 which was 23% of the total.

From the above, it was confirmed that the PyII introduction rate into the Lys residue is high.

Figure 7:
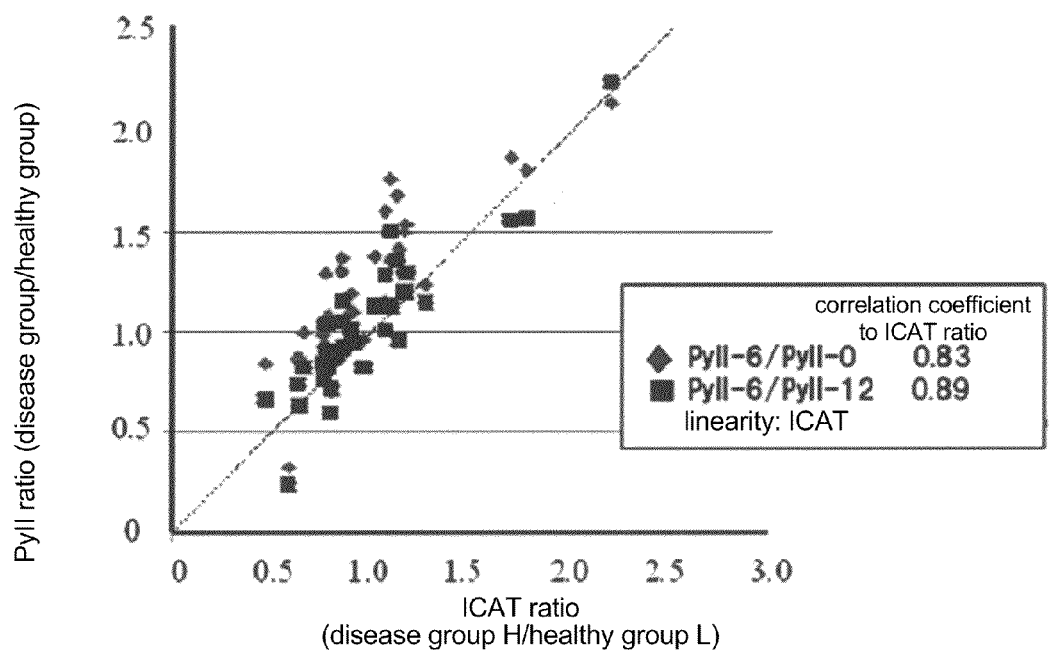
FIG. 7 shows the results of comparative experiment of the quantification accuracy of cICAT reagent and PyII reagent.

The quantification accuracy was compared between the cICAT reagent and the PyII reagent. The results are shown in FIG. 7. 1) The quantification ratio with PyII reagent matched well with the cICAT quantification ratio with the same sample.

As mentioned above, the validity of the utilization of PyII reagent for proteome analysis was evaluated and compared with commercially available reagent. As a result, (1) it was confirmed that comparison quantification analysis at a proteome level can be performed by utilizing PyII reagent and using plasma real sample as a target. (2) The PyII reagent (mass difference 6) showed less overlap between peptides as compared to Py reagent having a mass difference of 4, and the quantification accuracy was improved. (3) The results of comparison quantification using existing cICAT reagent in the same sample showed high agreement.

Experimental Example 1

Confirmation of Labeling of Cell Protein Extract with PyII Reagent by Fluorescence Two-Dimensional Electrophoresis (DIGE Method)

As a target of proteome analysis, quantitative comparison of the total protein amount of cells and tissues is also important besides the analysis of serum proteins. The kind of proteins present in cells and tissues is said to be not inferior to or exceed that of serum in number. Contrary to the proteins in blood, which are soluble in water, proteins in the cells show complicated physicochemical properties reflecting various manner of presence, such as solubility, membrane bindability, intranuclear protein, cytoskeletal protein and the like. While there is no all-purpose extraction method for comprehensively extracting and studying them, DIGE buffer is comparatively stable, and a solution called CLS (Cell Lysis Solution) was used for this experiment. The composition of CLS is 7M urea, 3M thiourea, 2% CHAPS, 0.2M borate buffer, pH 9.6.

In this experiment, HeLa cell, which is a human-derived cell line was used ($10^6$ cells per sample), precipitated cell mass was lysed by adding CLS (100 µL), placed on ice for 30 min, and centrifuged at 15,000 rpm for 20 min to recover total cell protein in the supernatant. Two groups thereof were prepared, the protein amount of the both was made equal, one of them was bound with green fluorescence dye Cy3 and the other was bound with red Cy5 while controlling the fluorescence amount so that about 2% on average of the total protein would be bound. It means about 2% on average of the lysine residue of any protein was labeled with a fluorescence dye. When equal amounts of the both were mixed and developed by 2D-DIGE method, and the distribution of fluorescence dye was detected by a laser fluorescence scanner, many fluorescence spots were detected on a transparent gel plate. Since Cy3 and Cy5 have different fluorescence properties, the fluorescence of Cy3 and the fluorescence of Cy5 could be observed with distinction. The both fluorescences could also be superimposed. When the same protein was fluorescence-labeled with Cy3 and Cy5, mixed and applied to two-dimensional electrophoretic separation, a spot was made at the same position and the spot where fluorescences were superimposed became a mixed color of yellow (FIG. 8, left Figure, spot in the square right below). The protein labeled with Cy5 was further labeled with PyII reagent. That is, Cy5 labeled protein lysed with CLS (pH 9.6) was labeled with 10 mM PyII at 50° C. for 3 hr. Equal amounts of the PyII-labeled protein and a Cy3-labeled PyII-unlabeled protein were mixed, separated by two-dimensional electrophoresis, and two-colored fluorescence was detected by a fluorescence scanner. The results of the both fluorescences being superimposed are shown in the right Figure of FIG. 8. Green fluorescence spots of protein were distributed all over gel. Red fluorescence spots are moving in the molecular weight increasing direction (upper direction) in the vicinity of each spot. Since red fluorescence is observed in the vicinity of even a spot with a weak fluorescence (low protein content), the results are assumed to reflect an increase in the molecular weight due to PyII labeling.

From the above, it was shown that PyII labeling has an ability to label many of the proteins in the cells among the current labeling methods.

Example 9

Labeling of Dopamine with 7 Kinds of PyII Reagents Having Mass Difference 2

To standard dopamine (2.5 pmol) (2.5 µM dopamine-containing 0.05 M hydrochloric acid solution, 1 µl) was added 5% perchloric acid to the total amount of 10 µl. 2M phosphate K buffer (pH 12, 20 µl) was added to maintain the mixture at pH 9. 100 mM PyII reagent (1 µl) was added, and the mixture was incubated at 50° C. for 15 min to allow for reaction of PyII reagent (PyII-0, PyII-2, PyII-4, PyII-6, PyII-8, PyII-10, PyII-12) with dopamine. Thereafter, each reaction mixture was mixed.

Then, using a column having phenylboric acid (PBA) as a functional group (MonoSpin PBA, GL SCIENCES INC.), dopamine-PyII compound in the sample was purified. The sample was bound to PBA, washed with acetonitrile, then 100 mM phosphate K buffer (pH 8.0), and further with 0.5% trifluoroacetic acid-containing 5% acetonitrile solution, and eluted with 0.5% trifluoroacetic acid-containing 30% acetonitrile solution. The eluate was concentrated by a centrifugal concentrator under reduced pressure, passed through a filter having a pore size of 0.22 μm (DURAPORE PVDF 0.22 μm, MILLIPORE), and analyzed by nano LC/MS system.

Figure 9:
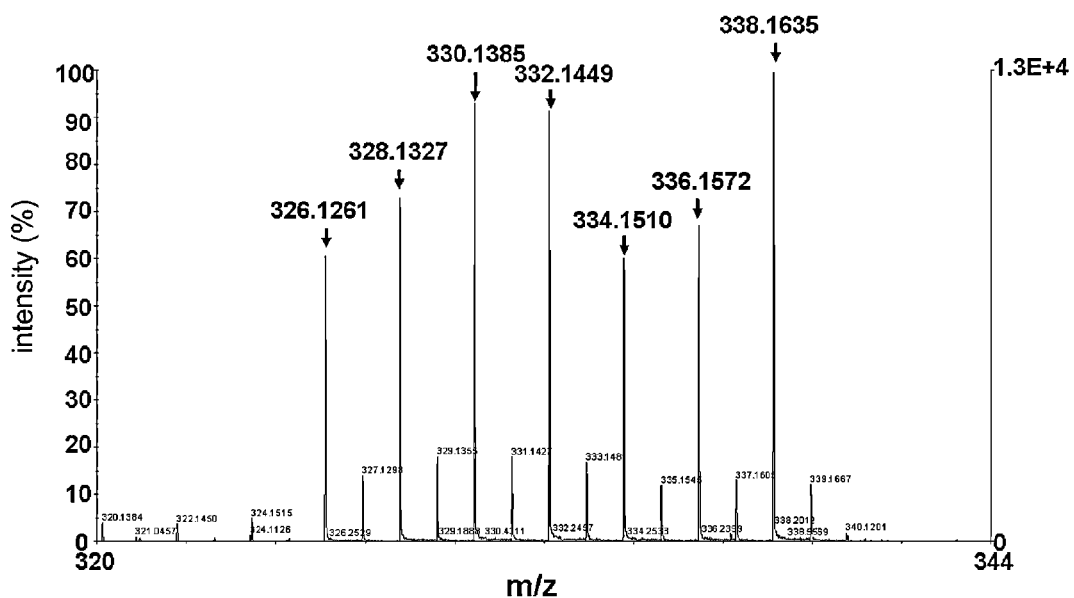
FIG. 9 shows the mass spectrum of dopamine labeled with each PyII compound.

The results are shown in FIG. 9. It was confirmed that 7 kinds of compounds having a mass difference of about 2 were produced from mass 326.1 to 338.2.

Experimental Example 2

Generation of Calibration Curve for Dopamine Measurement Using PyII Reagent

A calibration curve of standard dopamine (1250 fmol, 625 fmol, 313 fmol, 0 fmol) was produced. The 1250 fmol standard dopamine was reacted with PyII-12, 625 fmol was reacted with PyII-10, 313 fmol was reacted with PyII-8, and 0 fmol was reacted with PyII-0. As the internal standard, 500 fmol 3,4-dihydroxybenzylamine (DHBA) was used. 5% Perchloric acid was added to the standard dopamine solution (containing 500 fmol DHBA) to the total amount of 10 μl. Thereafter, according to the method of Example 9, the PyII compound and dopamine in the sample were reacted, respective reaction mixtures were mixed and, according to the method of Example 9, purification by PBA, concentration under reduced pressure and filtration with filter, and analysis by nano LC/MS system were performed.

Figure 10:
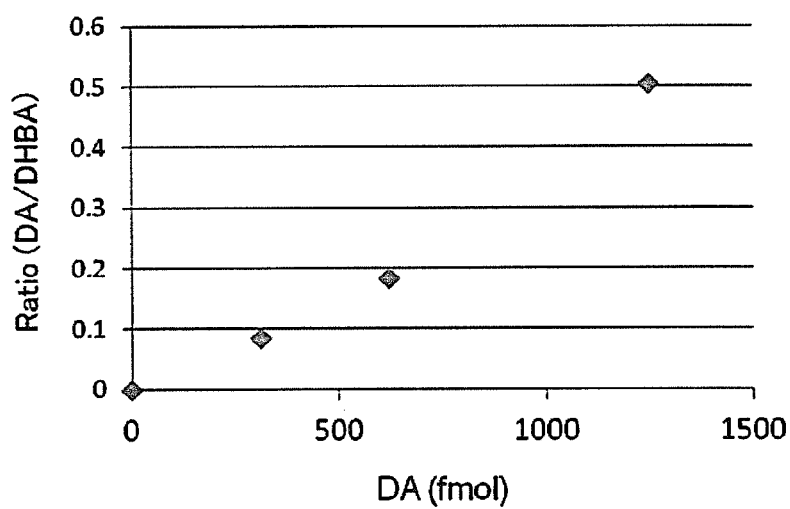
FIG. 10 shows a calibration curve prepared for the dopamine measurement using a PyII reagent.

When the obtained results were plotted with the ratio of dopamine and DHBA as the vertical axis, a linear relationship was obtained (FIG. 10). Therefore, it was clarified that dopamine can be quantified by PyII by using DHBA as the internal standard.

Example 10

Measurement of Dopamine Content of Rat Brain Using PyII Reagent

Microwave was irradiated on the head of rat (5 kW, 1.7 seconds) (microwave applicator, Muromachi Kikai Co., Ltd.), and the rat was fixed. After removal of the brain, a 30 μm-thick brain tissue section of a region including the striatum was produced by freezing microtome (CM3050S, Leica), and a brain tissue (square, 1 mm one side, thickness 30 μm) was obtained by laser microdissection (ASLMD, Leica). The volume of each collected section corresponds to 30 nl. Then, 5% perchloric acid (10 μl) and DHBA (500 fmol per sample) (500 nM DHBA-containing 0.05 M hydrochloric acid solution, 1 μl) as an internal standard substance were added, and the mixture was subjected to a deproteinization treatment by an acid extraction method. Thereafter, according to the method of Example 9, a PyII compound different for each site (PyII-0, PyII-2, PyII-4, PyII-6, PyII-8, PyII-10 or PyII-12) and dopamine in the sample were reacted, the reaction mixtures were mixed and, according to the method of Example 9, purification by PBA, concentration under reduced pressure and filtration with filter, and analysis by nano LC/MS system were performed.

Figure 11:
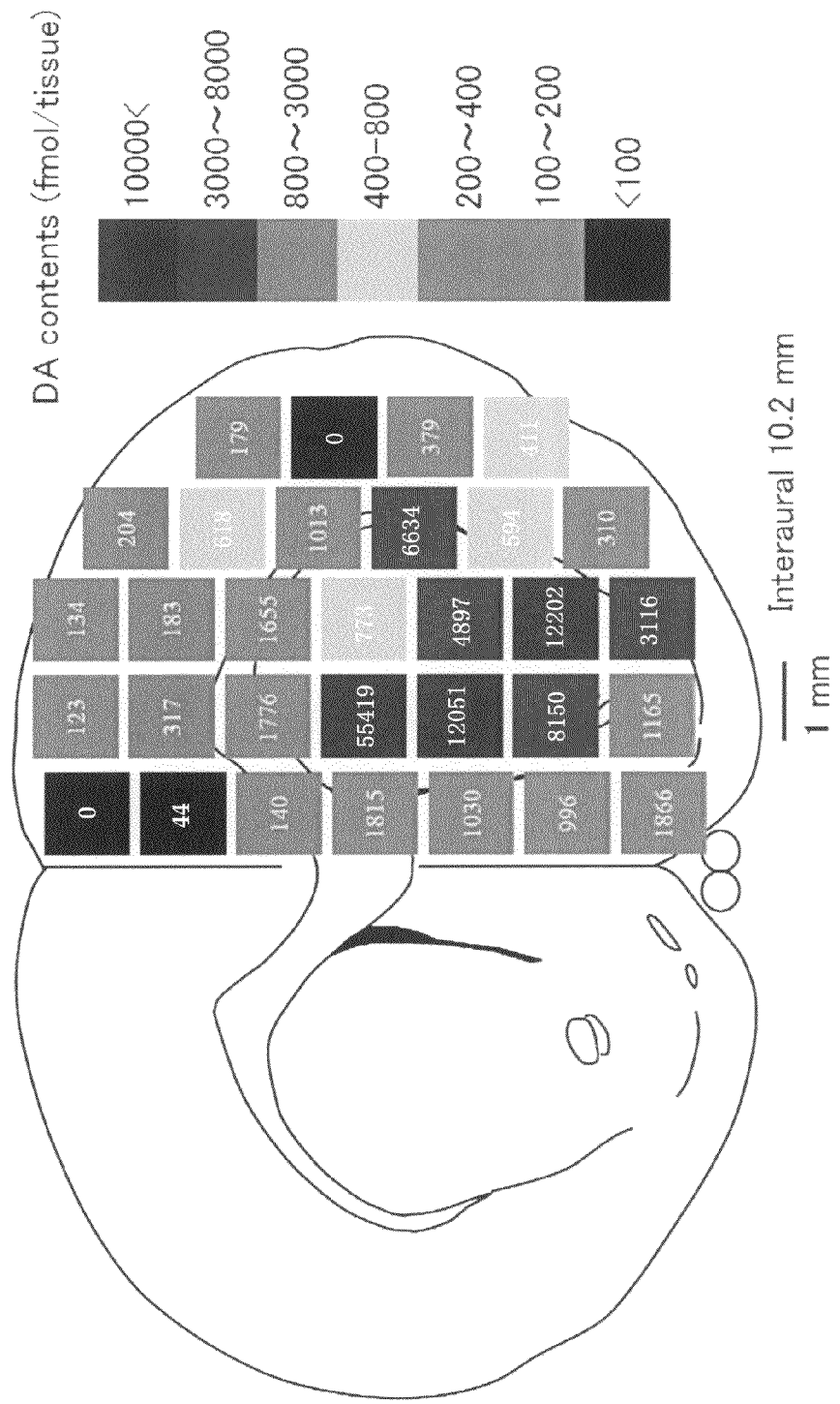
FIG. 11 shows the results of the measurement experiment of the dopamine content at a striatum level. Each square shows the site in the brain tissue and the number in the square shows the dopamine content at the site in a fmol unit.

The amount of dopamine in each region of the brain was calculated based on the obtained results of the mass spectrometry spectrum and the calibration curve of FIG. 10, and shown in FIG. 11. In the Figure, black squares show the region of the measured brain tissue sections corresponding to 30 nl, and the numbers therein show the content in fmol of dopamine contained in each brain tissue section. The results obtained show that the dopamine content is low in the cerebral cortex (123 and 317 fmol), and high in the striatum (996-1866 fmol). This is the same level as the conventional finding of dopamine measurement. From these results, it was confirmed that the content of dopamine in the brain tissue (30 nl) can be measured by the analysis method of the present invention using PyII reagent.

Example 11

Analysis Example of Amine and Amino Acid by PyII Reagent

To any one kind (2 μl) of 1 mM alanine, glutamic acid, glycine, γ-aminobutyric acid (GABA), ornithine, dopamine, noradrenaline, and serotonin standard solution (dissolved in 0.05M hydrochloric acid solution) were added 50 mM sodium borate buffer (pH 10.2, 10 μl), 70 mM PyII reagent (mixture of equal amounts of 10 mM PyII-0, PyII-2, PyII-4, PyII-6, PyII-8, PyII-10 and PyII-12, 2 μl), and distilled water (6 μl) to the total amount of 20 μl, and the mixture was incubated by heating at 50° C. for 60 min. After completion, 1M hydrochloric acid (2 μl) was added, the mixture was further diluted 100-fold with 0.05M hydrochloric acid solution, and 1 μl thereof was introduced into nano LC/MS, and MS analysis was conducted.

LC conditions were monolith-type MonoCap for FastFlow (0.05 mm ID×150 mmL, GL Sciences Inc.) as a separation column, C18-Monolith trap column (0.05 mm ID×150 mmL, GL Sciences Inc.) as a trap column, flow 200 nl/min, mobile phase A) formic acid/water/acetonitrile (0.1:98:2), B) formic acid/water/acetonitrile (0.1:2:98), and gradient elution was performed (i.e., A/B=98/2 (0 min)-2/98 (50 min)-2/98 (50.1-70 min)-98/2 (70.1-90 min)).

The setting of the mass measurement part was as follows. Ionization mode nano ESI (positive ionization), spray voltage 1600 V, detector voltage 1950 V, amount of counter nitrogen gas 0.8 L/min, scan range 100-500 m/z, and mass spectrometry recording time 50 min.

Figures 1, 12:
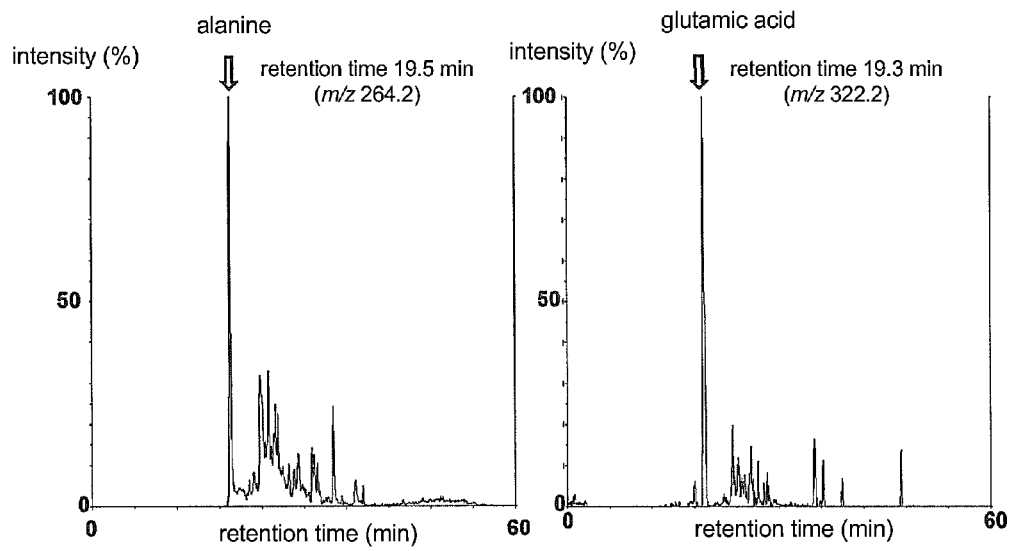
Figures 2, 12:
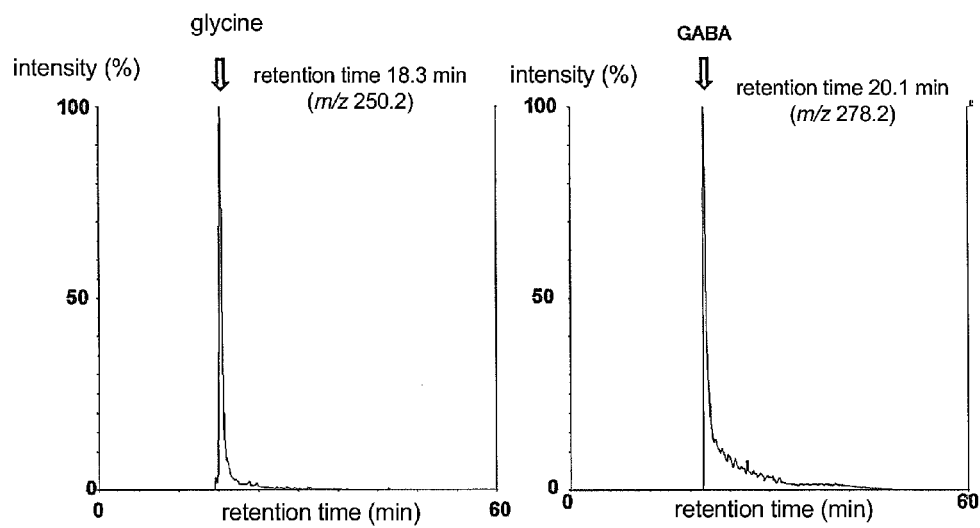
Figures 3, 12:
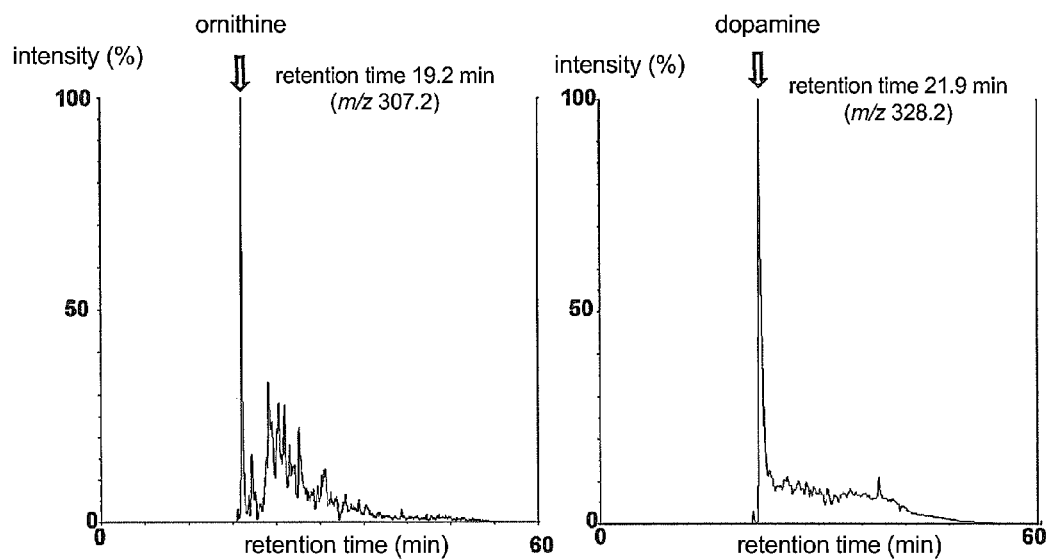
Figures 4, 12:
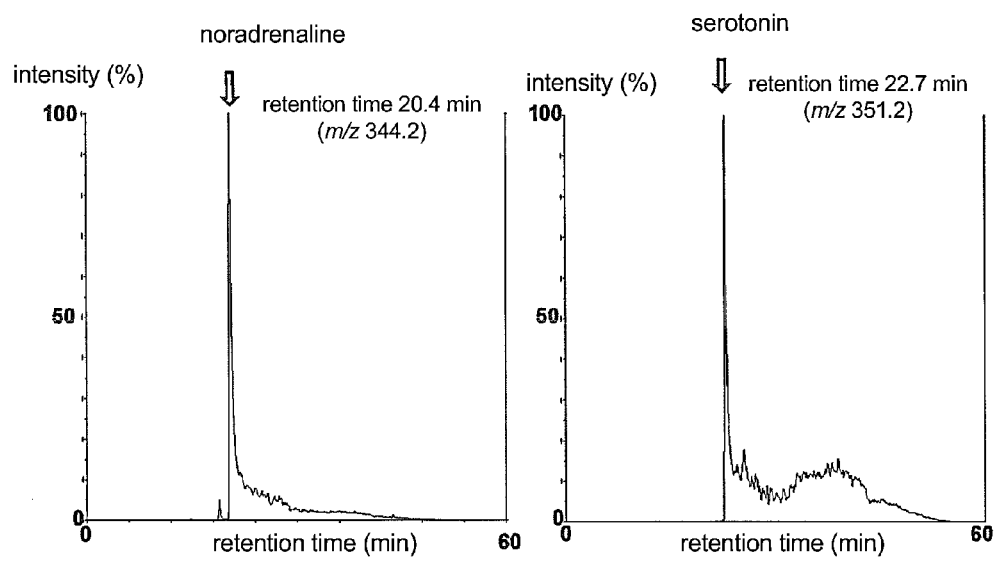
Figures 1, 13:
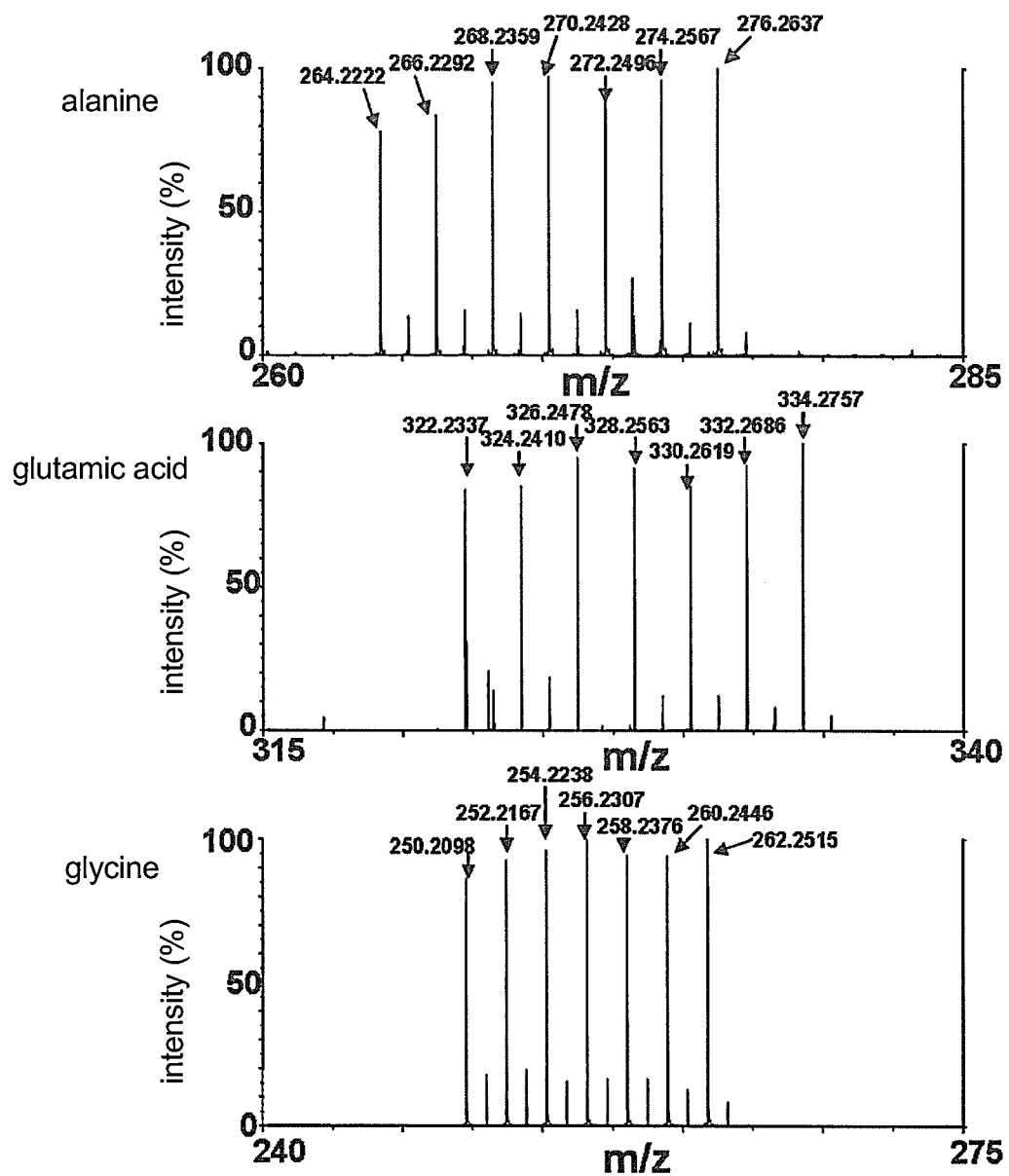
Figures 2, 13:
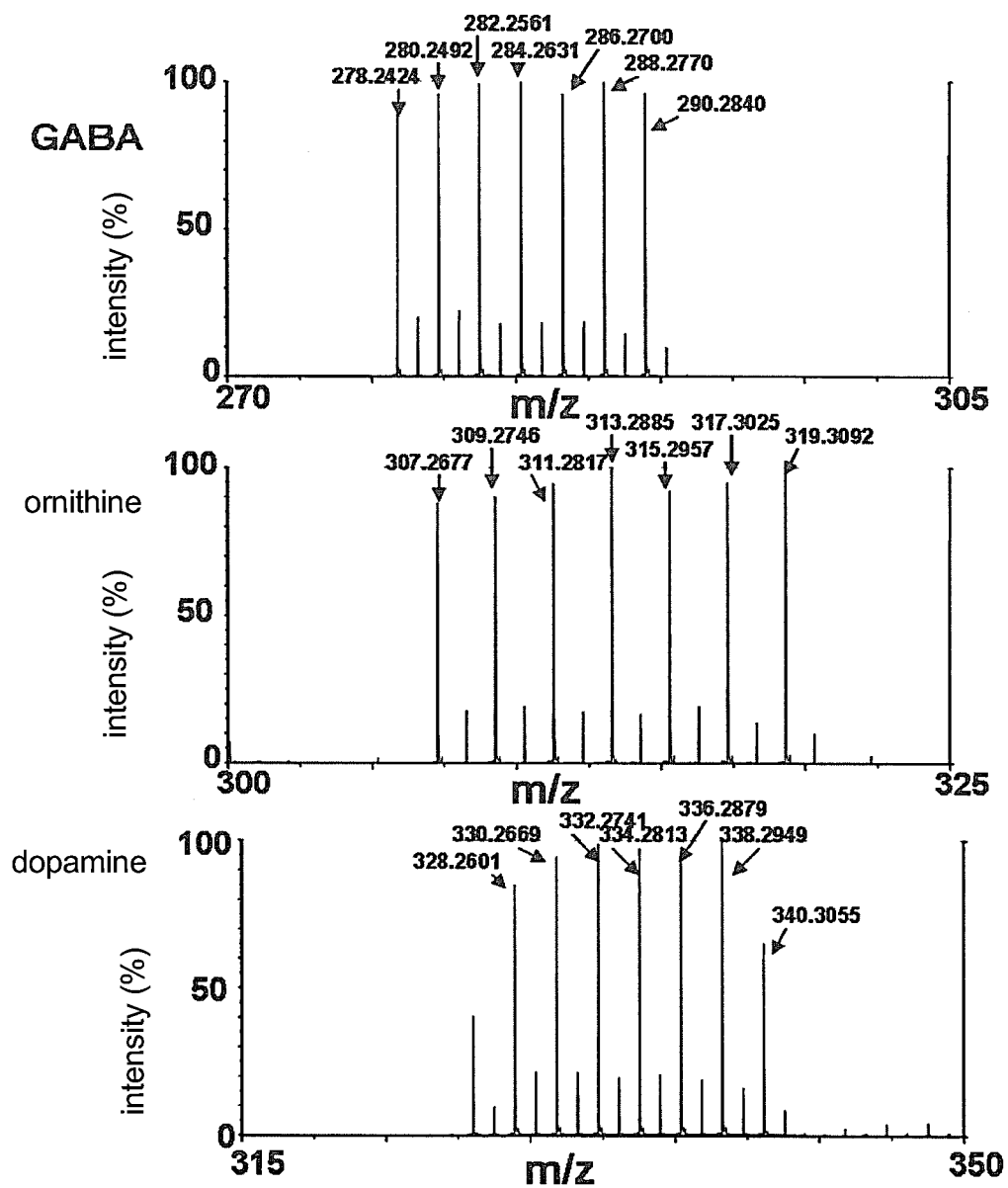
Figures 3, 13:
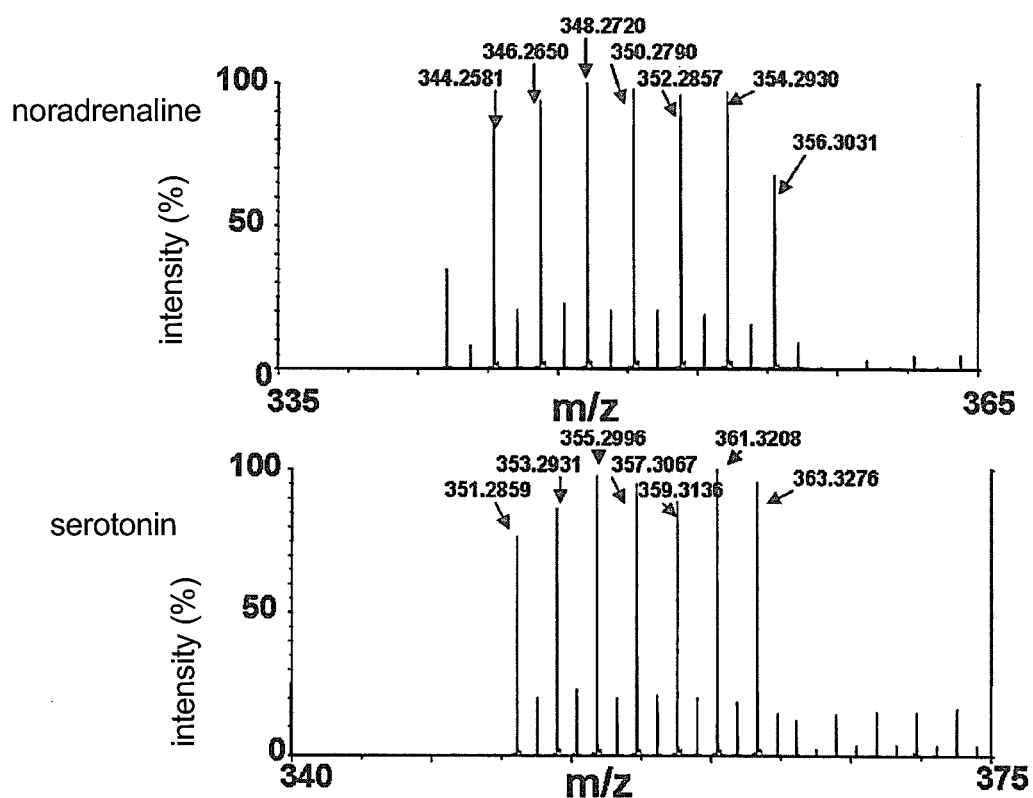

As for each PyII derivative measured at this time, ion chromatographs shown by mass M/z values are shown in FIG. 12, and mass spectra of the peaks in FIG. 12 are shown in FIG. 13. A single chromato peak and a mass peak identical with the calculated value were identified for each of the 8 kinds measured.

INDUSTRIAL APPLICABILITY

Since the isotope labeling compound of the present invention can provide plural compounds having a large mass difference (e.g., not less than 6) relative to each other, it can solve the problem of mutual interference between isotope peaks in comprehensive differential expression analysis of protein even with a peptide having any molecular weight. Particularly, since there is no conventional stable isotope-labeling reagent capable of providing 3 kinds of compounds having a mass difference of 6, it is conducible to an exceptionally efficient quantitative analysis of proteins.

The isotope labeling compound of the present invention also enables a simultaneous highly sensitive analysis of amino group-containing non-peptidic compounds contained in plural samples (e.g., 7 kinds). Furthermore, by automation using a trap column, a system capable of automatically performing a highly sensitive analysis at a femto mol level for 24 hr can be constructed.

This application is based on a patent application No. 2012-079110 filed in Japan (filing date: Mar. 30, 2012), the contents of which are incorporated in full herein.

The invention claimed is:

1. A compound represented by the formula (I):

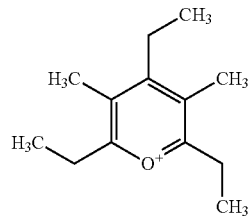
(I)

or a salt thereof.

2. The compound according to claim 1, wherein the formula (I) has one or more carbon atoms having a mass number of 13, or a salt thereof.

3. The compound according to claim 1, which is one compound selected from the group consisting of PyII-0, PyII-2, PyII-4, PyII-6, PyII-8, PyII-10 and PyII-12 represented by the formulas (II):

(II)

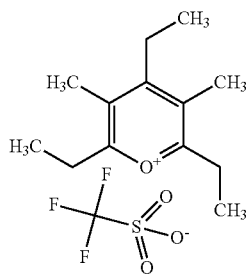
PyII-0

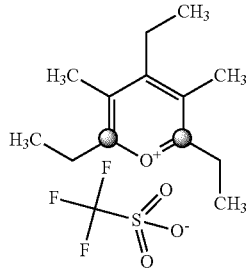
PyII-2

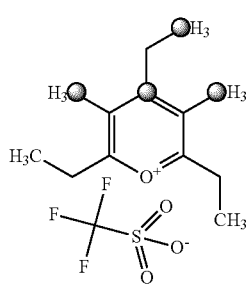
PyII-4

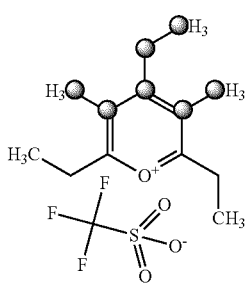
PyII-6

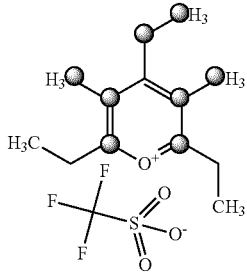
PyII-8

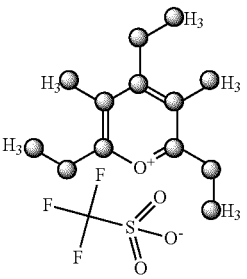
PyII-10

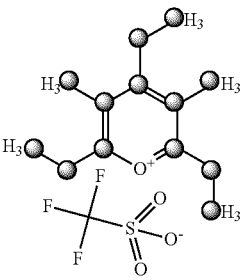
PyII-12 wherein carbon atoms shown by black balls have a mass number of 13, or a salt thereof.

4. A kit for quantifying an amino group-containing target substance in a biological sample by using a mass spectrometer, which comprises, as a labeling compound, two or more compounds having a mutually different mass due to isotope labeling, which are represented by the formula (I):

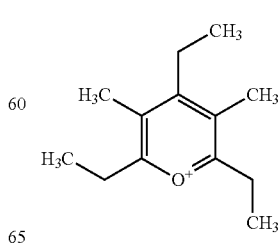
(I)

or a salt thereof.

5. The kit according to claim 4, comprising two or more compounds represented by the formula (I) having a mass difference of not less than 6 or a salt thereof, wherein the target substance is a protein.

6. The kit according to claim 5, comprising
a compound represented by the formula (I), which does not contain a carbon atom having a mass number of 13,
a compound represented by the formula (I), which has 6 carbon atoms having a mass number of 13, and
a compound represented by the formula (I), which has 12 carbon atoms having a mass number of 13,
or a salt thereof.

7. The kit according to claim 6, comprising PyII-0, PyII-6 and PyII-12 represented by the formula (III):

(III)

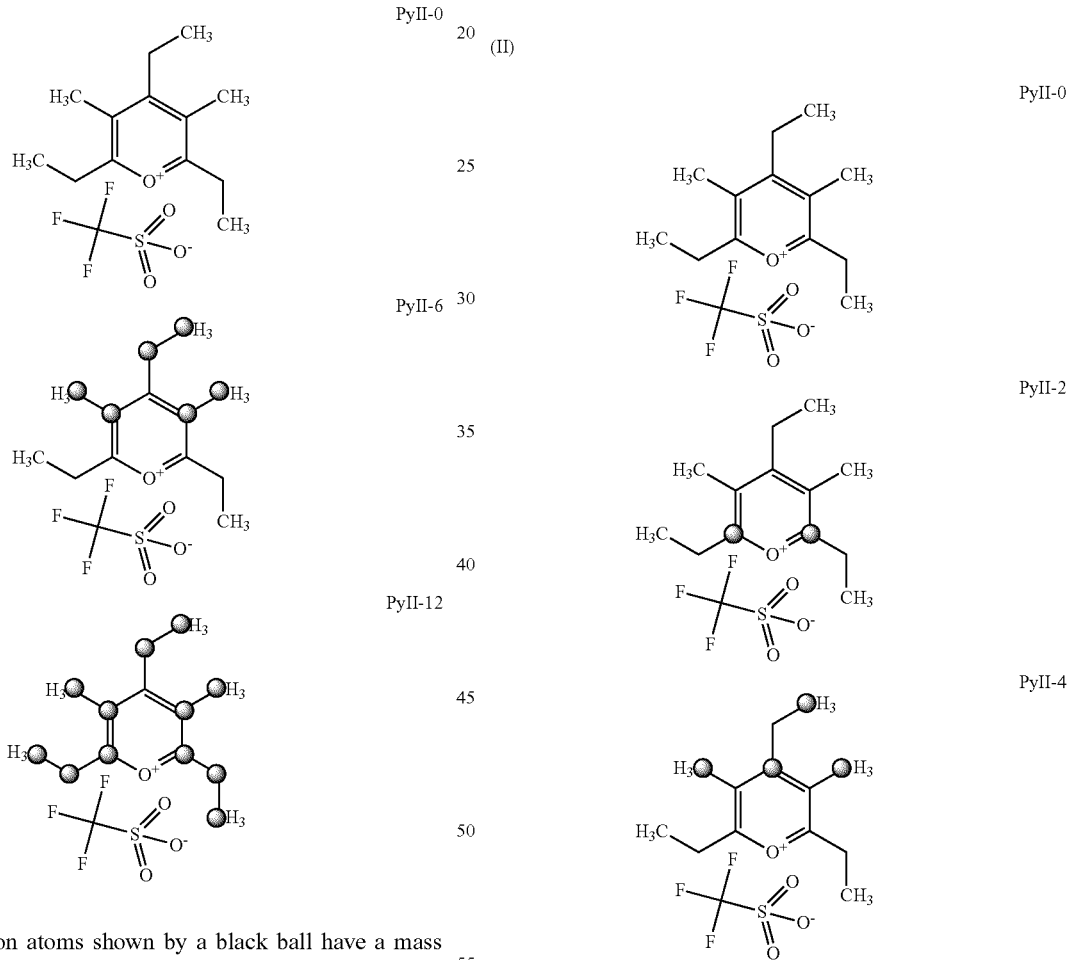

wherein carbon atoms shown by a black ball have a mass number of 13.

8. The kit according to claim 4, comprising two or more compounds represented by the formula (I) having a mass difference of two or more, or a salt thereof, wherein the target substance is an amino group-containing non-peptidic compound.

9. The kit according to claim 8, comprising two or more compounds selected from the group consisting of
a compound represented by the formula (I), which does not contain a carbon atom having a mass number of 13,
a compound represented by the formula (I), which has 2 carbon atoms having a mass number of 13,
a compound represented by the formula (I), which has 4 carbon atoms having a mass number of 13,
a compound represented by the formula (I), which has 6 carbon atoms having a mass number of 13,
a compound represented by the formula (I), which has 8 carbon atoms having a mass number of 13,
a compound represented by the formula (I), which has 10 carbon atoms having a mass number of 13, and
a compound represented by the formula (I), which has 12 carbon atoms having a mass number of 13,
or a salt thereof.

10. The kit according to claim 9, comprising two or more compounds selected from the group consisting of PyII-0, PyII-2, PyII-4, PyII-6, PyII-8, PyII-10 and PyII-12 represented by the formulas (II):

(II)

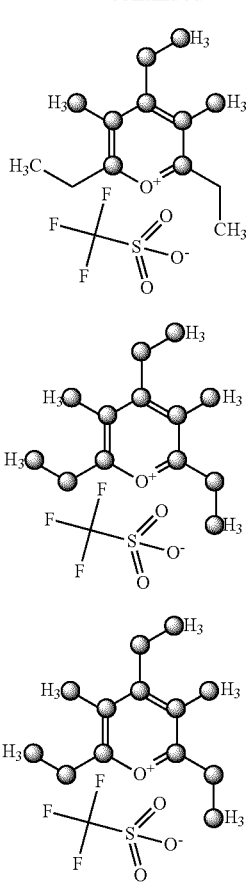

wherein carbon atoms shown by a black ball have a mass number of 13.

11. A method of quantitatively analyzing an amino group-containing target substance in two or more biological samples by using a mass spectrometer, comprising
(1) a step of preparing two or more biological samples to be subjected to an analysis,
(2) a step of labeling a target substance in samples prepared by using, as a labeling compound, two or more compounds having a mutually different mass due to isotope labeling, which are represented by the formula (I):

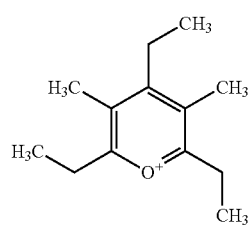

(I)

or a salt thereof, to confer a mass difference to the target substance between the samples,
(3) a step of preparing a mixture from all samples subjected to the labeling, and
(4) a step of subjecting the mixture to mass spectrometry, determining a presence ratio of the target substance in the mixture based on the ratio of peak intensity in mass spectrum of a target substance mutually having a mass difference due to labeling, and determining a quantitative ratio of the target substance between samples subjected to the preparation of the mixture, from the obtained presence ratio and the mixing ratio of the samples in step (3).

12. The method according to claim 11, wherein the target substance is an amino group-containing non-peptidic compound.

13. The method according to claim 12, wherein the labeling compound comprises two or more compounds represented by the formula (I) having a mass difference of 2 or more, or a salt thereof.

14. The method according to claim 13, wherein the labeling compound comprises two or more compounds selected from the group consisting of
a compound represented by the formula (I), which does not contain a carbon atom having a mass number of 13,
a compound represented by the formula (I), which has 2 carbon atoms having a mass number of 13,
a compound represented by the formula (I), which has 4 carbon atoms having a mass number of 13,
a compound represented by the formula (I), which has 6 carbon atoms having a mass number of 13,
a compound represented by the formula (I), which has 8 carbon atoms having a mass number of 13,
a compound represented by the formula (I), which has 10 carbon atoms having a mass number of 13, and
a compound represented by the formula (I), which has 12 carbon atoms having a mass number of 13,
or a salt thereof.

15. The method according to claim 14, wherein the labeling compound comprises two or more compounds selected from the group consisting of PyII-0, PyII-2, PyII-4, PyII-6, PyII-8, PyII-10 and PyII-12 represented by the formulas (II):

(II)

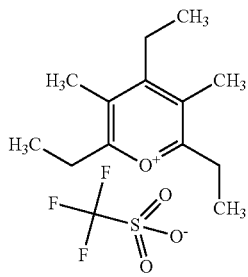

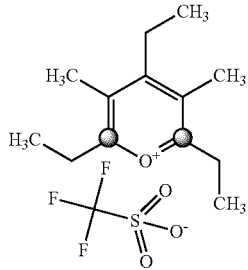

-continued

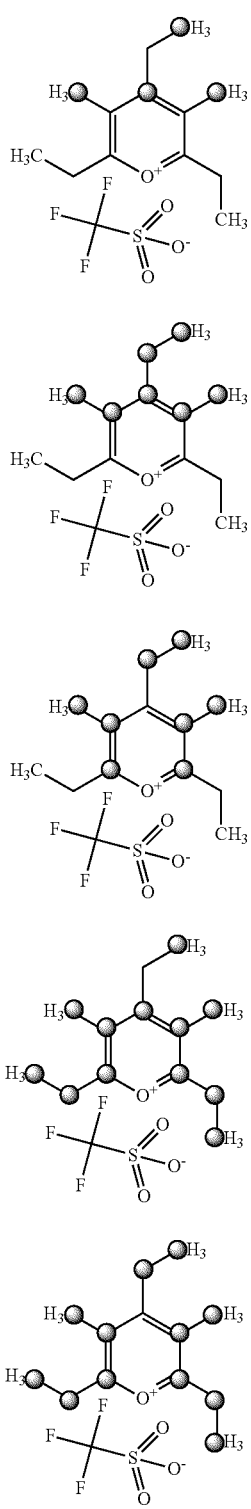

wherein carbon atoms shown by a black ball have a mass number of 13.

16. The method according to claim 11, wherein
one of the samples prepared in step (1) is the internal standard sample containing a target substance at a known concentration, and the determination of the presence ratio in step (4) comprises determining a ratio of a peak intensity of a target substance derived from each sample other than the internal standard sample and a target substance derived from the internal standard sample.

17. A method of quantitatively analyzing a protein in two or more biological samples by using a mass spectrometer, comprising (1) a step of preparing two or more biological samples to be subjected to an analysis, (2) a step of labeling a protein in samples prepared by using, as a labeling compound, two or more compounds having a mutually different mass due to isotope labeling, which are represented by the formula (I):

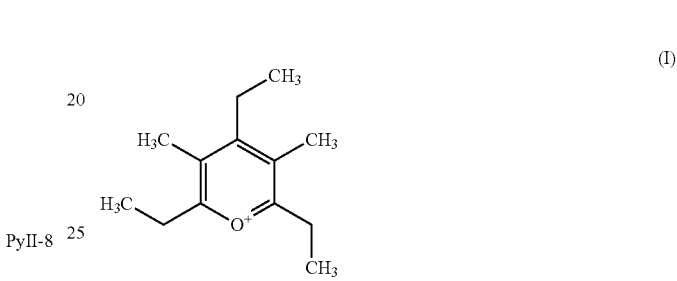

or a salt thereof, to confer a mass difference to the same protein between the samples, (3) a step of preparing a mixture from all samples subjected to the labeling, (4) a step of digesting the protein in the mixture with a protease to give a peptide, (5) a step of subjecting the obtained peptide to mass spectrometry, and determining a presence ratio of the peptide in the mixture based on the ratio of peak intensity in mass spectrum of the peptide mutually having a mass difference due to labeling, and (6) a step of identifying a protein from which the peptide having the determined presence ratio derives, and determining a quantitative ratio of the protein between samples subjected to the preparation of the mixture, from the presence ratio and the mixing ratio of the samples in step (3).

18. The method according to claim 17, wherein the labeling compound comprises two or more compounds represented by the formula (I) having a mass difference of 6 or more, or a salt thereof.

19. The method according to claim 18, wherein the labeling compound comprises
a compound represented by the formula (I), which does not contain a carbon atom having a mass number of 13,
a compound represented by the formula (I), which has 6 carbon atoms having a mass number of 13, and
a compound represented by the formula (I), which has 12 carbon atoms having a mass number of 13
or a salt thereof, and the protein in 3 biological samples is quantitatively analyzed.

20. The method according to claim 19, wherein the labeling compound comprises PyII-0, PyII-6 and PyII-12 represented by the following formulas (III):

(III)

PyII-0

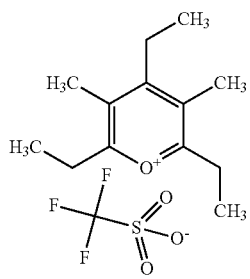

PyII-6

PyII-12

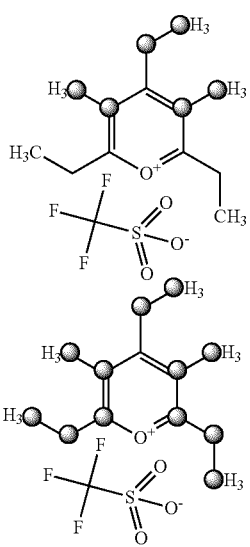

wherein carbon atoms shown by a black ball have a mass number of 13.

21. The method according to claim 17, wherein one of the samples prepared in step (1) is the internal standard sample obtained by mixing all other prepared samples, and the determination of the presence ratio in step (5) comprises determining a ratio of a peak intensity of a peptide derived from each sample other than the internal standard sample and a peptide derived from the internal standard sample.

22. A method of producing a compound of the formula (I) or a salt thereof, comprising condensing 3-ethyl-3-pentanol or 3-ethyl-2-pentene with anhydrous propionic acid in the presence of an anhydrous acid to give a compound of the formula (I):

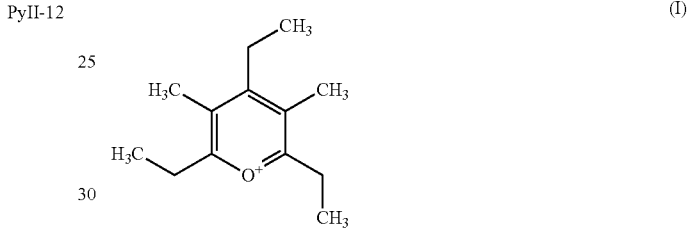

(I)

or a salt thereof.

* * * * *